(12) United States Patent
Ishizaki et al.

(10) Patent No.: US 6,251,960 B1
(45) Date of Patent: Jun. 26, 2001

(54) PROCESS FOR PRODUCTION OF WATER ABSORBENT RESIN

(75) Inventors: Kunihiko Ishizaki, Suita; Hisanobu Obara, Himeji; Nobuyuki Harada, Suita; Yoshihiro Motono; Koji Miyake, both of Himeji, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/343,460

(22) Filed: Jun. 30, 1999

Related U.S. Application Data

(62) Division of application No. 08/687,377, filed on Aug. 2, 1996, now Pat. No. 5,985,944.

(30) Foreign Application Priority Data

Dec. 8, 1994 (JP) ............................. 6-305185
Mar. 24, 1995 (JP) ............................. 7-065427

(51) Int. Cl.[7] ............................................. C08J 9/28
(52) U.S. Cl. ......................................... 521/72; 521/64
(58) Field of Search ......................... 521/64, 72

(56) References Cited

U.S. PATENT DOCUMENTS

| | | | |
|---|---|---|---|
| 4,703,067 | 10/1987 | Mikita et al. | 521/63 |
| 4,808,637 | 2/1989 | Boardman et al. | 521/50.5 |
| 4,839,395 | 6/1989 | Masamizu et al. | 521/56 |
| 5,118,719 | 6/1992 | Lind | 521/92 |
| 5,154,713 | 10/1992 | Lind | 604/358 |
| 5,314,420 | 5/1994 | Smith et al. | 604/358 |
| 5,328,935 | 7/1994 | Van Phan et al. | 521/64 |
| 5,338,766 | 8/1994 | Phan et al. | 521/63 |
| 5,399,591 | 3/1995 | Smith et al. | 521/53 |
| 5,462,972 | * 10/1995 | Smith et al. | 521/53 |
| 5,830,543 | 11/1998 | Miyake et al. | 428/35.2 |
| 5,856,370 | 1/1999 | Chmelir | 521/128 |

FOREIGN PATENT DOCUMENTS

| | | |
|---|---|---|
| 2267094 | 11/1993 | (GB) . |
| 46-18488 B1 | 5/1971 | (JP) . |
| 57-192356 | 11/1982 | (JP) . |
| 64-26545 | 1/1989 | (JP) . |
| 3-503059 | 7/1991 | (JP) . |
| 5-70597 | 3/1993 | (JP) . |
| WO 95/02002 | 1/1995 | (WO) . |
| WO 95/17455 | 6/1995 | (WO) . |

* cited by examiner

*Primary Examiner*—Morton Foelak
(74) *Attorney, Agent, or Firm*—Kubovcik & Kubovcik

(57) ABSTRACT

A water-absorbent resin is produced by dispersing a solid blowing agent having an average particle diameter within a range of from 1 $\mu$m to 100 $\mu$m in an aqueous monomer solution containing an unsaturated monomer and a cross-linking agent, and then polymerizing the unsaturated monomer. The water-absorbent resin has excellent water absorption characteristics, such as improved dispersion and absorption rate of aqueous fluid, enhanced water retention capacity and dry touch, lower water-soluble component content, and lower residual monomer content. When a water-absorbent resin composition using the water-absorbent resin is used for, for example, a sanitary material, it is possible to improve the absorption rate and water retention capacity, and prevent leakage of fluid from the sanitary material.

26 Claims, 6 Drawing Sheets

PROCESS FOR PRODUCTION OF WATER ABSORBENT RESIN

This application is a division of application Ser. No. 08/687,377, filed Aug. 2, 1996 U.S. Pat. No. 5,985,944.

FIELD OF THE INVENTION

The present invention relates to water-absorbent resins suitable for use in absorbent articles, for example, sanitary materials (body fluid absorbent articles) such as paper diapers (disposable diapers), sanitary napkins, so-called incontinence pads (articles for incontinent person), wound protecting material and wound healing material, building material, water retentive material for soil, drip absorbing and freshness retentive materials for food, and waterproof material. The present invention also relates to a process for producing such water-absorbent resins, and water-absorbent resin compositions using the water-absorbent resins.

BACKGROUND OF THE INVENTION

In recent years, water-absorbent resins for absorbing body fluids such as urine, sweat, and blood are widely used as a constituent element of sanitary materials such as paper diapers, sanitary napkins, incontinence pads, wound protecting material, and wound healing material. Such water-absorbent resins are utilized not only as sanitary materials, but also applied to various uses to absorb and retain water and absorb moisture, for example, building material, water retentive material for soil, drip absorbing and freshness retentive materials for food, and waterproof material.

Known water absorbing resins include partially neutralized and cross-linked acrylic acid (Japanese Publication for Unexamined Patent Applications No. (Tokukaisho) 55-84304, 55-108407, and 55-133413, and U.S. Pat. No. 4,654,039), hydrolyzed starch-acrylonitrile graft polymer (Japanese Publication for Examined Patent Application No. (Tokukosho) 49-43995, neutralized starch-acrylic acid graft polymer (Japanese Publication for Unexamined Patent Application No. (Tokukaisho) 51-125468), saponified vinyl acetate-acrylate copolymer (Japanese Publication for Unexamined Patent Application No. (Tokukaisho) 52-14689), hydrolyzed acrylonitrile copolymer or acrylamide copolymer, or cross-linked acrylonitrile copolymer and acrylamide copolymer (Japanese Publication for Unexamined Patent Application No. (Tokukaisho) 53-15959), cross-linked carboxymethyl cellulose, and cross-linked cationic monomer (Japanese Publication for Unexamined Patent Applications No. (Tokukaisho) 58-154709 and 58-154710), cross-linked isobutylene-maleic anhydride copolymer material, cross-linked copolymer of 2-acrylamido-2-methylpropane sulfonic acid and acrylic acid, cross-linked polyethyleneoxide, and cross-linked copolymer of methoxypolyethylene glycol and acrylic acid.

All of the water-absorbent resins are in the form of particles or powder having a particle diameter of around 0.01 mm to 5 mm. The absorption rate of the water-absorbent resin is generally determined by the particle diameter. There is a tendency that the absorption rate of each particle increases as the particle diameter becomes smaller ("Polymers" Vol. 36, page 614, Polymer Association, 1987).

However, in actual, as the particle diameter becomes smaller, the liquid permeability for allowing aqueous fluids, for example, body fluids, to flow between the particles, is lowered. Namely, a so-called gel blocking phenomenon occurs. Therefore, when using the water-absorbent resin, it is necessary to select an optimum particle diameter by considering the absorption rate and the liquid permeability. The tendency of causing a gel blocking phenomenon becomes higher as the absorption rate of the water-absorbent resin increases. The main causes of the gel blocking phenomenon are a decrease in the void space and an increase in tack between particles after being swelled, under pressure.

In order to improve the water absorption characteristics of the water-absorbent resin, particularly, the absorption rate, various production methods and modification methods of water-absorbent resins have been proposed as shown below. More specifically, as the production and modification methods of water-absorbent resins, for example, the following two methods have been proposed. ① Application of secondary cross-linking treatment, i.e., improving the cross-link density in the vicinity of a particle surface. ② Increasing the particle surface area by granulation, foaming, formation of pores, or the like.

The method ① includes methods which use the following materials as a surface cross-linking agent. Namely, a method using polyhydric alcohol; a method using a polyglycidyl compound, a polyaziridine compound, a polyamine compound and a polyisocyanate compound; a method using glyoxal; a method using polyvalent metal salt; a method using a silane coupling agent; a method using a mono epoxy compound; a method using a polymer containing an epoxy group; a method using an epoxy compound and a hydroxy compound; and a method using alkylene carbonate.

For instance, the following methods were also proposed. A method in which a cross-linking reaction is performed under the presence of inactive inorganic powder (U.S. Pat. No. 4,587,308). A method in which a cross-linking reaction is performed under the presence of dihydric alcohol. A method in which a cross-linking reaction is performed under the presence of water and an ether compound. A method in which a cross-linking reaction is performed under the presence of alkylene oxide added monohydric alcohol, organic acid salt, or lactam. A method in which more than one kind of cross linking agents having different solubility parameters are used. Moreover, the methods for improving the cross-link density in the vicinity of the particle surface are disclosed in U.S. Pat. No. 4,666,983, No. 5,140,076 and No. 5,229,466, and Japanese Publication for Unexamined Patent Applications No. (Tokukaisho) 59-62665 and No. (Tokukaihei) 5-508425.

As the method ②, for example, a method using a blowing agent during polymerization or cross-linking was proposed. The method using a blowing agent includes, for example, methods in which a cross-linked structure is introduced into a linear water-soluble polymer while performing neutralization using a blowing agent such as carbonate (U.S. Pat. No. 4529,739 and No. 4,649,164), methods in which carbonate salt is added to monomers (Japanese Publication For Examined Patent Applications No. (Tokukosho) 62-34042, No. (Tokukohei) 2-60681, and No. (Tokukohei) 2-54362, and U.S. Pat. No. 5,118,719, No. 5,154,713 and No. 5,314,420), a method in which monomers are polymerized using a microwave under the presence of carbonate salt (U.S. Pat. No. 4,808,637), methods in which an organic solvent having a boiling point within a range of from 40° C. to 150° C. is added to a specified monomer and then polymerized (Japanese Publication For Unexamined Patent Application No. (Tokukaisho) 59-18712, and U.S. Pat. Nos. 4,552,938, No. 4,654,393 and No. 4,703,067), and methods in which a hydrophobic organic solvent is added and polymerized under specified pressure (U.S. Pat. No. 5,328,935 and No. 5,338,766). Additionally, methods in which a blowing agent is added after polymerizing monomers were also proposed (Japanese Publication For Unexamined Patent Applications No. (Tokukaisho) 56-13906, No. (Tokukaisho) 57-182331, and No. (Tokukaisho) 57-208236).

Furthermore, the following methods were also proposed. A method in which a polarity is given to particles using a microwave (WO No. 91/02552). Methods in which fine particles are made into secondary particles by granulation (WO No. 93/24153, U.S. Pat. No. 5,002,986, No. 5,300,565, No. 5,140,076 and No. 4,732,968).

With the use of the methods ① and ②, it is possible to improve the absorption rate of the water-absorbent resin to some extent.

However, the water-absorbent resin prepared by cross-linking cannot achieve a high absorption rate which is required when it is used, for example, in sanitary materials. In addition, the water-absorbent resin prepared by cross-linking while foaming a linear polymer does not have sufficient absorbent capacity (water retention capacity), and requires a high cost. Whereas the porous water-absorbent resin prepared by foaming while polymerizing monomers is excellent in terms of the absorption rate and cost. However, it is difficult to control the timing of foaming, and cannot achieve a uniform pore diameter. Thus, these water-absorbent resins failed to sufficiently improve various characteristics related to the dispersion of aqueous fluid, water-soluble component content, residual monomer content, and dry touch (these characteristics will be explained later).

More specifically, the water-absorbent resins obtained by the above-mentioned production method or modification method have such disadvantage that the mutual balance of conflicting characteristics, such as the dispersion of aqueous fluid, the water-soluble component content, and dry touch, is not satisfactory. Namely, the above-mentioned conventional water-absorbent resins do not have sufficiently improved water absorption characteristics, and cannot provide high water absorption characteristics which are required when used, for example, in sanitary materials.

An object of the production method and modification method is to produce a water-absorbent resin capable of promptly absorbing aqueous fluid when the water-absorbent resin comes into contact with the aqueous fluid. Therefore, these methods are designed without substantially considering the water absorption characteristics that are required of the water-absorbent resin when the water-absorbent resin is used in a sanitary material, particularly, when a large amount of water-absorbent resin is used in sanitary material to reduce the thickness of the sanitary material.

In the sanitary material using a large volume of the water-absorbent resin, it is necessary to improve the absorption. However, if the absorption rate is increased, the gel blocking phenomenon tends to occur. In order to reduce the incidence of the gel blocking phenomenon, for example, an attempt has been made to improve the elasticity of gel. However, if the elasticity of gel is improved, the water retention capacity of the water-absorbent resin is lowered. Therefore, even if the water-absorbent resin having improved absorption rate and elasticity of gel is used in the sanitary material, it is hard to say that the sanitary material is prevented from leakage. Thus, there is a demand for a water-absorbent resin capable of keeping various characteristics such as absorption rate and water retentive ability, and achieving improved dispersion of aqueous fluid between particles after absorption, that is a characteristic conflicting the above characteristics.

The present invention was carried out to solve the above conventional problems. An objective of the present invention is to provide a water-absorbent resin having excellent water absorption characteristics such as the dispersion and absorption rate of aqueous fluid, water retentive ability and dry touch, lower water-soluble component content, and lower residual monomer content. Another objects of the present invention to provide a process for producing the water-absorbent resins, and a water-absorbent resin composition using the water-absorbent resin.

DETAILED DESCRIPTION OF THE INVENTION

In order to achieve the above objects, the present inventors fully studied water-absorbent resins, process for producing the water-absorbent resins, and water-absorbent resin compositions. It was found as a result of study that a water-absorbent resin obtained by dispersing a solid blowing agent in the form of particles having an average particle diameter within a range of from 1 $\mu$m to 100 $\mu$m in an aqueous monomer solution containing an unsaturated monomer and a cross-linking agent and then polymerizing the unsaturated monomer, has excellent water absorption characteristics, such as dispersion and absorption rate of aqueous fluid, water retention capacity and dry touch, and lower water-soluble component content and lower residual monomer content. It was also found as a result of study that, when a water-absorbent resin composition using the water-absorbent resin is applied to, for example, a sanitary material, the absorption rate and the water retention capacity are enhanced, thereby preventing the sanitary material from leakage. The present invention was completed based on these findings.

Namely, in order to achieve the above objects, the process for producing a water-absorbent resin of the present invention is characterized by dispersing a solid blowing agent having an average particle diameter within a range of from 1 $\mu$m to 100 $\mu$m in an aqueous monomer solution containing an unsaturated monomer and a cross-linking agent and then polymerizing the unsaturated monomer.

With this process, it is possible to industrially produce water-absorbent resins having excellent water absorption characteristics, such as dispersion and absorption rate of aqueous fluid, water retention capacity and dry touch, and lower water-soluble component content and lower residual monomer content, in a simplified manner at low costs.

Moreover, in order to achieve the above objects, the water-absorbent resin of the present invention is characterized by that it is porous with an average pore diameter ranging from 10 $\mu$m to 500 $\mu$m, and has an absorbent capacity of not lower than 25 g/g 60 minutes after the initiation of water absorption under pressure, a water-soluble component content of not higher than 15 weight percent, and a residual monomer content of not higher than 500 ppm.

Furthermore, in order to achieve the above object, the water-absorbent resin composition of the present invention is characterized by that the water retention capacity is not lower than 20 g/g, the absorption rate is not higher than 120 seconds, and the liquid permeability under pressure is not higher than 200 seconds.

This structure can provide a water-absorbent resin and a water-absorbent resin composition having excellent liquid permeability and dispersion under pressure, without causing a gel blocking phenomenon, and improved absorption rate and absorbent capacity.

The following description will discuss the present invention in detail.

The unsaturated monomer used as a starting material in the present invention is soluble in water. Examples of the unsaturated monomer are:

- monomers containing an acid group, such as acrylic acid, β-acryloyloxypropionic acid, methacrylic, acid, crotonic acid, maleic acid, maleic anhydride, fumaric acid, itaconic acid, cinnamic acid, sorbic acid, 2-(meth)acryloylethane sulfonic acid, 2-(meth) acryloylpropane sulfonic acid, 2-(meth) acrylamido-2-methylpropane sulfonic acid, vinyl sulfonic acid, styrene sulfonic acid, allyl sulfonic acid, vinyl phosphonic acid and 2-(meth)acryloyloxyethyl phosphate, and alkaline metal salts and alkaline earth metal salts, ammonium salts, and alkyl amine salts thereof;
- dialkyl amino alkyl(meth)acrylates, such as N,N-dimethylaminoethyl(meth)acrylate and N,N-dimethylaminopropyl (meth) acrylate, and quaternary compounds thereof (for example, a reaction product produced with alkylhalide, and a reaction product produced with dialkyl sulfuric acid);
- dialkyl amino hydroxyalkyl(meth)acrylates, and quaternary compounds thereof;
- N-alkyl vinyl pyridine halide;
- hydroxyalkyl(meth)acrylates, such as hydroxymethyl (meth)acrylate, 2-hydroxyethyl (meth)acrylate, and 2-hydroxypropyl (meth)acrylate;
- acrylamide, methacrylamide, N-ethyl (meth) acrylamide, N-n-propyl(meth)acrylamide, N-isopropyl(meth)acrylamide, N,N-dimethyl (meth)acrylamide, 2-hydroxyethyl (meth)acrylate, 2-hydroxypropyl (meth)acrylate, methoxypolyethylene glycol (meth)acrylate, polyethylene glycol mono(meth)acrylate, vinylpyridine, N-vinylpyrrolidone, N-acryloyl piperidine, and N-acryloyl pyrrolidine;
- vinyl acetate; and
- alkyl (meth)acrylates, such as methyl (meth)acrylate, and ethyl (meth)acrylate. These monomers may be used individually, or in combination.

Among the above-exemplified monomers, unsaturated monomers containing an acrylate monomer as a chief constituent are preferred because the resulting water-absorbent resins have significantly improved water absorption characteristics. Here, the acrylate monomers means acrylic acids and/or water-soluble salts of acrylic acids. The water-soluble salts of acrylic acids are alkaline metal salts, alkaline earth metal salts, ammonium salts, hydroxy ammonium salts, amine salts and alkyl amine salts of acrylic acids having a neutralization rate within a range of from 30 mole percent to 100 mole percent, more preferably within a range of from 50 mole percent to 99 mole percent. Among the exemplified water-soluble salts, sodium salt and potassium salt are more preferred. These acrylate monomers may be used individually or in combination.

When the unsaturated monomer contains an acrylate monomer as a chief constituent, the amount of monomers other than the acrylate monomer is preferably less than 40 weight percent, more preferably less than 30 weight percent, and most preferably less than 10 weight percent of the total unsaturated monomer. By using the monomers other than the acrylate monomer in the above mentioned ratio, the water absorption characteristics of the resulting water-absorbent resin are further improved, and the water-absorbent resin can be obtained at further reduced costs.

As a cross-linking agent used for polymerizing the unsaturated monomer in the present invention, for example, the following compounds are listed. Compounds having a plurality of vinyl groups in a molecule. Compounds having at least one vinyl group in a molecule and at least one functional group reactive with a carboxyl group in the unsaturated monomer. Compounds having in a molecule a plurality of functional groups reactive with the carboxyl group. These cross-linking agents may be used individually, or in combination.

Examples of the compounds having a plurality of vinyl groups in a molecule are N,N'-methylene bis(meth)acrylamide, (poly)ethylene glycol di(meth)acrylate, (poly)propylene glycol di(meth)acrylate, trimethylolpropane tri(meth)acrylate, trimethylolpropane di(meth)acrylate, glycerine tri(meth)acrylate, glycerine acrylate methacrylate, ethyleneoxide denaturated trimethylolpropane tri(meth)acrylate, pentaerythritol tetra(meth)acrylate, dipentaerythritol hexa(meth)acrylate, N,N-diallyl acrylamide, triallyl cyanurate, triallyl isocyanurate, triallyl phosphate, triallylamine, diallyloxy acetate, N-methyl-N-vinyl acrylamide, bis(N-vinyl carboxylic amide), and poly(meth)aliloxy alkanes such astetraallyloxy ethane.

As the compound having at least one vinyl group in a molecule and at least one functional group reactive with the carboxylic group, for example, ethylene unsaturated compounds having at least one hydroxyl group, epoxy group or cationic group can be used. Example of such compounds are glycidyl (meth)acrylate, N-methylol acrylamide, and dimethylaminoethyl(meth)acrylate.

As the compound having a plurality of functional groups reactive with the carboxyl group in a molecule, for example, compounds having at least two hydroxyl groups, epoxy groups, cationic groups or isocyanate groups can be used. Example of such compounds are (poly)ethylene glycol diglycidyl ether, glycerol diglycidyl ether, ethylene glycol, polyethylene glycol, propylene glycol, glycerin, pentaerythritol, ethylenediamine, ethylene carbonate, polyethylene imine, and ammonium sulfate.

Among the exemplified cross-linking agents, preferred compounds are water-soluble compounds having a plurality of vinyl groups in a molecule, such as N,N'-methylene bis(meth)acrylamide, (poly)ethylene glycol di (meth) acrylate, (poly) propylene glycol di (meth) acrylate, trimethylolpropane tri (meth) acrylate, trimethylolpropane di (meth) acrylate, glycerine tri (meth) acrylate, glycerine acrylate methacrylate, ethyleneoxide denaturated trimethylolpropane tri(meth)acrylate, pentaerythritol tetra(meth)acrylate, dipentaerythritol hexa(meth)acrylate, triallyl cyanurate, triallyl isodyanurate, triallyl phosphate, triallylamine, and poly(meth)alyloxy alkane.

The amount of the cross-linking agent with respect to the unsaturated monomer varies depending on a combination of unsaturated monomer and cross-linking agent. However, the cross-linking agent is used in an amount ranging preferably from 0.0001 weight parts to 10 weight parts, more preferably from 0.001 weight parts to 5 weight parts, most preferably from 0.01 weight parts to 2 weight parts, based on 100 parts by weight of the unsaturated monomer. When the amount of cross-linking agent exceeds 10 weight parts, such unfavorable results are shown that the absorbent capacity of the resulting water-absorbent resin is lowered, and foaming by a blowing agent, to be described later, becomes insufficient. On the other hand, when the amount of cross-linking agent is less than 0.0001 weight parts, such unfavorable results are exhibited that the absorption rate and the gel strength of the resulting water-absorbent resin are lowered, the water soluble component content increases, and the control of foaming by a blowing agent is difficult. If the unsaturated monomer is polymerized without using a blowing agent, the water absorption characteristics of the resulting water-absorbent resin and various properties of the water-absorbent resin after absorption become unsatisfactory.

When polymerizing the unsaturated monomer under the presence of a cross-linking agent, it is preferred to use an aqueous solution as the unsaturated monomer and the cross-linking agent in order to improve the water absorption characteristics of the resulting water-absorbent resin and to achieve efficient foaming by a blowing agent. Namely, water is preferably used as a solvent. The concentration of the unsaturated monomer in the aqueous solution (hereinafter referred to as the aqueous monomer solution) is within a range of preferably from 20 weight percent to 65 weight percent, more preferably from 25 weight percent to 60 weight percent, most preferably from 30 weight percent to 45 weight percent. If the concentration of the unsaturated monomer is less than 20 weight percent, the water-soluble component content in the resulting water-absorbent resin may increase, and the absorption rate may not be improved because foaming by the blowing agent is insufficient. On the other hand, if the concentration of the unsaturated monomer exceeds 65 weight percent, it may be difficult to control the reaction temperature and the foaming by the blowing agent.

It is also possible to use water and an organic solvent soluble in water together as a solvent for the aqueous monomer solution. Examples of the organic solvent are methyl alcohol, ethyl alcohol, acetone, dimethyl sulfoxide, ethylene glycol monomethyl ether, glycerin., (poly)ethylene glycol, (poly)propylene glycol, and alkylene carbonate. These organic solvents may be used individually, or in combination.

In this case, the amount of the organic solvent is preferably controlled so that the average particle diameter of the blowing agent dispersed is within a range of from 1 $\mu$m to 100 $\mu$m. More specifically, the amount of the organic solvent is preferably not higher than 40 percent by weight of water, more preferably not higher than 20 weight percent, most preferably not higher than 10 weight percent.

The blowing agent used when polymerizing the unsaturated monomer in the present invention is in particle form, and is a compound which is insoluble or slightly soluble in water and in the organic solvent and is solid at normal temperatures. Example of such a blowing agent are:

organic compounds, such as azodicarbonamide, azobisisobutyronitrile, barium azodicarboxylate, dinitrosopentamethylenetetramine, 4,4'-oxybis(benzen sulfonyl hydrazide), p-toluenesulfonyl hydrazide, diazoaminobenzene, N,N'-dimethyl-N,N'-dinitrosoterephthalamide, nitrourea, acetone-p-toluenesulfonyl hydrazone, p-toluenesulfonyl azide, 2,4-toluenedisulfonyl hydrazide, p-methylurethane benzene sulfonyl hydrazide, trinitroso trimethylene triamine, p-toluenesulfonyl semicarbazide, oxalyl hydrazide, nitroguanidine, hydroazocarbonamide, trihydrazino triamine, azobis formamide, benzenesulfonyl hydrazide, benzene-1,3-disulfonyl hydrazide, diphenyl sulfone-3,3'-disulfonyl hydrazide, 4,4'-oxybis (benezene sulfonyl hydrazide), sulfone hydrazide, malonic acid and salts thereof, and carbamic acid and salts thereof;

acrylic acid salts of azo-compounds containing an amino group, represented by general formula (1)

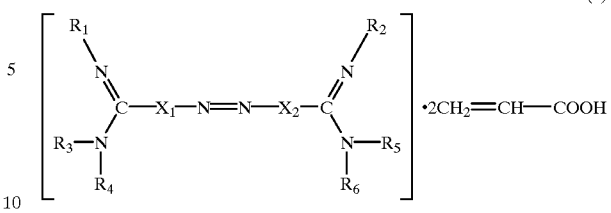

(1)

(wherein $X_1$ and $X_2$ independently represent an alkylene group having 1 to 4 carbons, $R_1$, $R_2$, $R_3$, $R_4$, $R_5$, and $R_6$ independently represent a hydrogen atom, alkyl group having 1 to 4 carbons, aryl group, allyl group or benzyl group), or general formula (2)

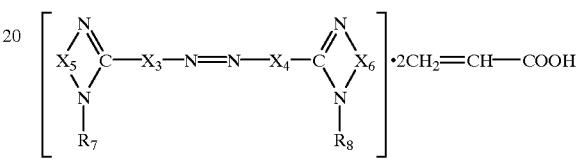

(2)

(wherein $X_3$ and $X_4$ independently represent an alkylene group having 1 to 4 carbons, $X_5$ and $X_6$ independently represent an alkylene group having 2 to 4 carbons, and $R_7$ and $R_8$ independently represent a hydrogen atom or alkyl group having 1 to 4 carbons); and inorganic compounds, such as carbonates including sodium bicarbonate, ammonium carbonate, ammonium bicarbonate, ammonium nitrite, basic magnesium carbonate, and calcium carbonate. These blowing agents may be used individually, or in combination. Among the exemplified blowing agents, acrylic acid salts of azo-compound containing an amino group are particularly preferred. The acrylic acid salt of the azo-compound containing an amino group can be evenly dispersed in the aqueous monomer solution in a still state while retaining a predetermined average particle diameter without using a dispersing agent such as a surface active agent and water-soluble polymer, and does not cause sedimentation, floatation nor separation. Moreover, the acrylic acid salts of azo-compounds containing an amino group exhibit excellent dispersion properties with respect to acrylate monomers.

The acrylic acid salts of azo-compounds containing an amino groups represented by general formula (1) or (2) include, but are not necessarily limited to, 2,2'-azobis(2-methyl-N-phenylpropionamidine) diacrylate, 2,2'-azobis[N-(4-chlorophenyl)-2-methyl propion amidine] diacrylate, 2,2'-azobis[N-(4-hydroxyphenyl)-2-methyl propion amidine] diacrylate, 2,2'-azobis[2-methyl-N-(phenylmethyl)-propion amidine]diacrylate, 2,2'-azobis[2-methyl-N-(2-propenyl)-propion amidine]diacrylate, 2,2'-azobis(2-methyl propion amidine) diacrylate, 2,2'-azobis[N-(2-hydroxyethyl)-2-methylpropionamidine] diacrylate, 2,2'-azobis [2-(5-methyl-2-imidazolin-2-yl)propane] diacrylate, 2,2'-azobis[2-(2-imidazolin-2-yl)propane] diacrylate, 2,2'-azobis-[2-(4,5,6,7-tetrahydro-1H-1,3-diacepine-2-yl) propane] diacrylate,2,2'-azobis[2-(3,4,5,6-tetrahydropyrimidine-2-yl)propane] diacrylate, 2,2'-azobis [2-(5-hydroxy-3,4,5,6-tetrahydropyrimidine-2-yl)propane] diacrylate, and 2,2'-azobis{2-[1-(2-hydroxyethyl)-2- imidazoline-2-yl]propane} diacrylate. Among the above-exemplified acrylic acid salts of azo-compounds containing an amino group, 2,2'-azobis(2-methyl propion amidine) diacrylate is particularly preferred.

The acrylic acid salt of azo-compounds containing an amino group can be easily isolated by precipitating the acrylic acid salts in, for example, an aqueous monomer solution and then filtering. When precipitating the acrylic acid salts of azo-compound containing an amino group in an aqueous monomer solution, a poor solvent may be added or cooling may be performed, if necessary.

As the blowing agent, a blowing agent prepared beforehand may be added to the aqueous monomer solution, or a blowing agent may be prepared by dissolving a precursor of the blowing agent (hereinafter referred to as the blowing agent precursor) in the aqueous monomer solution, and then adding carbon dioxide gas and acrylic acid salt to the aqueous monomer solution, if necessary. Namely, it is possible to precipitate the blowing agent by reacting the blowing agent precursor with the carbon dioxide gas and acrylic acid salt in the aqueous monomer solution. A preferred acrylic acid salt is sodium acrylate. When the unsaturated monomer is an acrylate monomer, the unsaturated monomer can function as the acrylic acid salt.

The acrylic acid salts of azo-compounds containing an amino group function as both the blowing agent and the radical polymerization initiator. By polymerizing the unsaturated monomer under the presence of the acrylic acid salt of the azo-compound containing an amino group, it is possible to obtain a water-absorbent resin having further reduced water-soluble component content and residual monomer content. More specifically, by using the acrylic acid salt of the azo-compound containing an amino group, it is possible to obtain a water-absorbent resin containing the water-soluble component in an amount of not higher than 15 weight percent, preferably within a range of from 1 weight percent to 10 weight percent, and the residual monomers in an amount of not higher than 500 ppm, preferably not higher than 300 ppm, more preferably not higher than 100 ppm.

The amount of the blowing agent with respect to the unsaturated monomer is not particularly limited, and is suitably decided depending on a combination of the unsaturated monomer and the blowing agent. However, the blowing agent is used in an amount ranging preferably from 0.005 weight parts to 25 weight parts, more preferably from 0.01 weight parts to 5 weight parts, most preferably from 0.05 weight parts to 2.5 weight parts, based on 100 parts by weight of the unsaturated monomer. When the amount of the blowing agent is out of the above-mentioned ranges, the resulting water-absorbent resin may not have sufficient water absorption characteristics.

The average particle diameter of the blowing agent which is present in a dispersed state during polymerization is within a range of preferably from 1 $\mu$m to 100 $\mu$m, more preferably from 2 $\mu$m to 50 $\mu$m, most preferably from 3 $\mu$m to 40 $\mu$m. By setting the average particle diameter of the blowing agent within the above-mentioned range, it is possible of adjust the average pore diameter of the water-absorbent resin within a range of from 10 $\mu$m to 500 $\mu$m, more preferably from 20 $\mu$m to 400 $\mu$m, still more preferably from 30 $\mu$m to 300 $\mu$m, most preferably from 50 $\mu$m to 200 $\mu$m, thereby improving the water absorption characteristics of the water-absorbent resin (for example, the dispersion and absorption rate of the aqueous fluid). Namely, it is possible to set the average pore diameter of the water-absorbent resin within a desired range by setting the average particle diameter of the blowing agent.

If the average particle diameter of the blowing agent is smaller than 1 $\mu$m or if the blowing agent is dissolved in the aqueous monomer solution, the degree of foaming becomes insufficient, and the average pore diameter of the water-absorbent resin cannot be adjusted within the desired range. On the other hand, if the average particle diameter of the blowing agent is larger than 100 $\mu$m, the average pore diameter of the water-absorbent resin cannot be adjusted within the desired range. In addition, a decrease in the gel strength of the water-absorbent resin and an increase in the water-soluble component content unfavorably occur. The average particle diameter of the blowing agent in the aqueous monomer solution can be easily measured with a laser-type particle size distribution apparatus.

As the blowing agent precursor when the blowing agent is an inorganic compound, for example, calcium hydroxide and magnesium hydroxide are given.

When the blowing agent is acrylic acid salt of the azo-compound containing an amino group, the blowing agent precursor is hydrochloride of the azo-compound containing an amino group. Examples include 2,2'-azobis(2-methyl-N-phenyl propion amidine) dihydrochloride, 2,2'-azobis[N-(4-chlorophenyl)-2-methylpropion amidine] dihydrochloride, 2,2'-azobis[N-(4-hydroxyphenyl)-2-methylpropion amidine] dihydrochloride, 2,2'-azobis[2-methyl-N-(phenylmethyl)-propion amidine] dihydrochloride, 2,2'-azobis[2-methyl-N-(2-propenyl)-propion amidine] dihydrochloride, 2,2'-azobis(2-methyl propion amidine) dihydrochloride, 2,2'-azobis[N-(2-hydroxyethyl)-2-methylpropion amidine] dihydrochloride, 2,2'-azobis[2-(5-methyl-2-imidazoline-2-yl)propane] dihydrochloride, 2,2'-azobis[2-(2-imidazoline-2-yl)propane] dihydrochloride, 2,2'-azobis[2-(4,5,6,7-tetrahydro-1H-1,3-diacepine-2-yl) propane]dihydrochloride, 2,2'-azobis [2-(3,4,5,6-tetrahydropyrimidine-2-yl)propane] dihydrochloride, 2,2'-azobis[2-(5-hydroxy-3,4,5,6-tetrahydropyrimidine-2-yl) propane] dihydrochloride, and 2,2'-azobis{2-[1-(2-hydroxyethyl)-2-imidazoline-2-yl]propane} dihydrochloride. These dihydrochlorides of azo-compounds containing an amino group are heat decomposable azo polymerization initiators.

The hydrochloride of azo-compound containing an amino group causes sedimentation, floatation and separation if the solubility in the aqueous monomer solution is low. Therefore, if the hydrochloride of azo-compound containing an amino group is directly used as a blowing agent, a water-absorbent resin having excellent water absorption characteristics cannot be obtained.

The condition for producing the acrylic acid salt of azo-compound containing an amino group by reacting the hydrochloride of the azo-compound containing an amino group with an acrylic acid salt is not particularly limited, but the following conditions are preferred. It is preferred to arrange the pore diameter of the resulting water-absorbent resin to a desired size by freely setting the conditions and suitably adjusting the particle diameter during dispersion of the acrylic acid salt of the azo-compound containing an amino group.

Specifically, the set temperature is within a range of preferably from −10° C. to 50° C., more preferably from 0° C. to 40° C. As the acrylic acid salts, acrylic alkaline metal salts are preferred, and sodium acrylate is more preferred. The neutralization rate of the acrylic acid salt is preferably not lower than 50 mole percent, more preferably not lower than 70 mole percent. The concentration of the acrylic acid salt in the aqueous monomer solution is within a range of preferably from 20 weight percent to a saturated concentration, more preferably from 25 weight percent to the saturation concentration.

Moreover, when producing the acrylic acid salts of azo-compounds containing an amino group, it is desirable to agitate the aqueous monomer solution. By agitating the aqueous monomer solution at a rate not lower than 10 rpm, more preferably at rates ranging from 20 rpm to 10,000 rpm, it is possible to prepare the acrylic acid salt of azo-compound containing an amino group having a substantially uniform particle diameter within a short time. The prepared acrylic acid salt of azo-compound containing an amino group can be directly used for the polymerization of an unsaturated monomer without the necessity of isolation.

As a method of producing acrylic acid salts of azo-compounds containing an amino group in an aqueous monomer solution, i.e., a method of dispersing acrylic acid salts of azo-compounds containing an amino group in an aqueous monomer solution, for example, the following two methods are given. A method of producing an aqueous monomer solution by adding the hydrochloride of azo-compound containing an amino group to an acrylic acid salt having a neutralization rate of 100 percent to prepare an acrylic acid salt of the azo-compound containing an amino group, and then mixing an unsaturated monomer, such as an acrylic acid which has not been neutralized, a cross-linking agent, and a solvent if necessary, with the acrylic acid salt. A method of producing an aqueous monomer solution in which an acrylic acid salt of azo-compound containing an amino group is dispersed by adding hydrochloride of the azo-compound containing an amino group, and an acrylic acid salt if necessary, to an aqueous monomer solution which is prepared beforehand. The latter method is more preferred because it can more efficiently produce the acrylic acid salt of the azo-compound containing an amino group with a uniform, particle diameter. It is also possible to adjust the concentration of the unsaturated monomer in the aqueous monomer solution to a desired level by adding a solvent such as water to the aqueous monomer solution after producing the acrylic acid salt of the azo-compound containing an amino group.

The following description will discuss a process for producing a water-absorbent resin according to the present invention.

The water-absorbent resin of the present invention is obtained by dispersing a blowing agent in an aqueous monomer solution and then polymerizing an unsaturated monomer (aqueous solution polymerization).

The method of dispersing the blowing agent in the aqueous monomer solution is not particularly limited. Examples include: a method of dispersing a blowing agent by adding the blowing agent to an aqueous monomer solution; a method of dispersing a blowing agent by adding a blowing agent precursor to an aqueous monomer solution and then producing and dispersing the blowing agent in the aqueous monomer solution; and a method of dispersing a blowing agent by producing an aqueous monomer solution by adding an unsaturated monomer, a cross-linking agent and a blowing agent to a solvent such as water and dispersing the blowing agent. Among these methods, a preferred method is the method of dispersing a blowing agent by adding a blowing agent precursor to an aqueous monomer solution and then producing and dispersing the blowing agent in the aqueous monomer solution because this method produces a water-absorbent resin having a further improved water absorption characteristics. When dispersing the blowing agent, the aqueous monomer solution may be agitated, or may not be agitated.

However, when the blowing agent is an inorganic compound such as carbonate salt and the unsaturated monomer includes an acrylate monomer as a chief constituent, since the reactivity of the inorganic compound and the acrylate monomer is relatively high, it is difficult to disperse the inorganic compound in the aqueous monomer solution and control the particle diameter thereof. In this case, it is; desirable to disperse the inorganic compound in the aqueous monomer solution by using a dispersion stabilizer such as a surface-active agent and water-soluble polymer.

When the blowing agent is carbonate salt, preferred examples of the dispersion stabilizer are:

hydrophilic organic solvents, such as methyl alcohol, ethyl alcohol, propyl alcohol, butyl alcohol, acetonitrile, and dimethyl formamide;

water-soluble polymers, such as polyvinyl alcohol, starches and their derivatives, polygalacto mannan, cellulose including methyl cellulose, carboxymethyl cellulose and hydroxyethyl cellulose and their derivatives, polyalkylene oxides, polyacrylic acids, and polyacrylic acid salts;

anionic surface active agents, such as fatty acid salts of sodium oleate and potassium caster oil, alkylsulfuric ester salts of lauryl sodium sulfide and lauryl ammonium sulfide, alkylbenzene sulfonic acid salts including dodecyl benzene sodium sulfonic acid salt, alkyl naphthalene sulfonic acid salt, dialkyl sulfo-succinate, alkyl phosphate salt, and naphthalenesulfonic formalized condensation product, and polyoxyethylene alkyl sulfate salt;

nonionic surface active agents, such as polyoxyethylene alkyl ether, polyoxyethylene alkyl phenol ether, polyoxyethylene fatty acid ester, sorbitan fatty acid ester, polyoxy sorbitan fatty acid ester, polyoxyethylene alkylamine, fatty acid esters, and oxyethylene-oxypropylene block polymer;

cationic surface active agents, such as alkyl amine salts including lauryl amine acetate and stearyl amine acetate, quaternary ammonium salts including lauryl trimethyl ammonium chloride and stearyl trimethyl ammonium chloride; and amphoteric ionic surface active agents, such as lauryl dimethylamine oxide. However, it is not necessary to restrict the dispersion stabilizer to those mentioned above. Such dispersion stabilizers may be used individually, or in combination.

Among the above-exemplified dispersion stabilizers, it is preferred to use at least one kind of dispersion stabilizer selected from the group consisting of water-soluble polymer and surface active agent. It is more preferred to use both the water-soluble polymer and surface active agent. Among the water-soluble polymers, polyvinyl alcohol, starches and their derivatives, cellulose and the derivatives are preferred. The polyvinyl alcohol and hydroxyethyl cellulose are particularly preferred. Partially saponified polyvinyl alcohol is still more preferred. Among the surface active agents, anionic surface active agents and nonionic surface active agents are preferred. Nonionic surface active agents having an HLB of not lower than 7 are particularly preferred.

By adding such a dispersion stabilizer to the aqueous monomer solution, it is possible to evenly disperse an inorganic compound (blowing agent) such as carbonate in the aqueous monomer solution, and control the average particle diameter of the inorganic compound within a range of from 1 $\mu$m to 100 $\mu$m. The amount of the dispersion stabilizer with respect to the blowing agent is suitably set according to the combination of the blowing agent and the dispersion stabilizer. The amount of the dispersion stabilizer to be used is not necessarily limited, but is preferably no more than 5 weight parts based on 100 parts by weight of unsaturated monomer, and preferably no more than 500 weight parts, more preferably no more than 100 weight parts, still more preferably no more than 50 weight parts, most preferably no more than 10 weight parts based on 100 parts by weight of the blowing agent. More specifically, the amount of the dispersion stabilizer to be used is within a range preferably from 0.01 weight parts to 500 weight parts, more preferably from 0.05 weight parts to 100 weight parts, still more preferably from 0.5 weight parts to 50 weight parts, most preferably from 0.5 weight parts to 10 weight parts.

The unsaturated monomer in the aqueous monomer solution in which the blowing agent is dispersed can be polymerized by a known method. The polymerization method is not particularly limited, and various methods can be used. Examples include radical polymerization using a, radical polymerization initiator, irradiation-induced polymerization, electron radiation-induced polymerization, and ultraviolet-induced polymerization using a photosensitizer. Among these methods, radical polymerization is more preferred because this method can quantitatively and perfectly polymerize the unsaturated monomer.

As the radical polymerization, there are various Polymerization methods, such as aqueous solution polymerization, cast polymerization which is performed within a mold, thin-layer polymerization which is performed on a belt conveyer, polymerization which is performed while making generated hydrogel polymer into small pieces, reversed-phase suspension polymerization, reversed-phase emulsion polymerization, precipitation polymerization, and bulk polymerization. Among these polymerization methods, the aqueous solution polymerization which polymerizes the unsaturated monomer in the form of aqueous solution is more preferred because the polymerization temperature can be easily controlled.

The aqueous solution polymerization of the unsaturated monomer may be performed either continuously or batch-wise, or may be performed under suction, pressure, or atmospheric pressure. The polymerization is preferably performed in the flow of inactive gas, such as nitrogen, helium, argon, or carbonate gas.

When performing the aqueous solution polymerization, it is preferred to dissolve or disperse a radical polymerization initiator in an aqueous monomer solution in advance. Examples of the radical polymerization initiator include:

peroxides, such as ammonium persulfate, potassium persulfate, sodium persulfate, hydrogen peroxide, benzoyl peroxide, cumene hydroperoxide, and di-t-butyl peroxide;

redox initiators formed by combining the above-mentioned peroxides and reducing agents, such as sulfite, bisulfite, thiosulfate, formamidine sulfinic acid, and. ascorbic acid;

acrylic acid salts of azo-compound containing an amino group represented by general formula (1) or (2) above; and azo polymerization initiators, such as hydrochlorides of the azo-compound containing an amino group. These radical polymerization initiators may be used individually, or in combination. When the acrylic acid salt of azo-compound containing an amino group is used as the radical. polymerization imitator, it is more preferred to use a, redox initiator together with the acrylic acid salt.

The amount of the radical polymerization initiator with respect to the unsaturated monomer is varied depending on the combination of the unsaturated monomer and the radical polymerization initiator. However, the amount of the radical polymerization initiator to be used is within a range of preferably from 0.0005 weight parts to 5 weight parts, more preferably from 0.005 weight parts to 2.5 weight parts, based on 100 parts by weight of the unsaturated monomer. If the amount of the radical polymerization initiator is less than 0.0005 weight parts, the amount of unreacted unsaturated monomers increases, causing an unfavorable increase of the residual monomer content in the resulting water-absorbent resin. On the other hand, if the amount of the radical polymerization initiator exceeds 5 weight parts, an unfavorable increase of the water-soluble component content in the resulting water-absorbent resin occurs.

Although the temperature at the initiation of polymerization varies depending on the type of a radical. polymerization initiator used, it is preferably within a, range of from 0° C. to 40° C., more preferably from 10° C. to 30° C. Similarly, although the polymerization temperature during the reaction varies depending on the type of a radical polymerization initiator used, it is preferably within a range of from 40° C. to 120° C., more preferably from 50° C. to 110° C. If the temperature at the initiation of polymerization or the polymerization temperature during the reaction is outside of the above-mentioned range, unfavorable results may be exhibited, for example, the residual monomer content in the resulting water-absorbent resin increases, the control of foaming by a blowing agent becomes difficult, and the absorbent capacity of the water-absorbent resin is lowered because of an excessive self-cross-linking reaction.

The reaction time is not necessarily limited, but is preferably set according to the combination of the unsaturated monomer, cross-linking agent and radical polymerization initiator, or reaction conditions such as the reaction temperature. Moreover, the time between the dispersion of the blowing agent and the initiation of the polymerization of the unsaturated monomer is not necessarily limited, but a relatively short time is preferred.

When performing the aqueous solution polymerization, the aqueous monomer solution may be agitated or may not be agitated. However, in order to achieve efficient foaming by the blowing agent, it is desirable to keep the aqueous monomer solution at rest for at least a predetermined period of time during the reaction. Foaming by the blowing agent is more efficiently performed by keeping the aqueous monomer solution at rest after the initiation of polymerization until the polymerization rate reaches 10 percent, more preferably 30 percent, still more preferably 50 percent, most preferably until the end of polymerization. When using the acrylic acid salt of an azo-compound containing an amino group represented by general formula (1) or (2) above as the blowing agent, the polymerization may be carried out while performing agitation from the initiation of polymerization until the end of polymerization, i.e., the entire polymerization is performed under the agitated condition.

A hydrogel containing cells which is a (co)polymer of the unsaturated monomer is produced by the polymerization. More specifically, the hydrogel containing cells is produced as follows. The unsaturated monomer is (co)polymerized, a cross-linking reaction by the cross-linking agent and foaming by the blowing agent proceed, and holes (voids) are formed in the (co)polymer.

The hydrogel containing cells is chopped into pieces of a size ranging from about 0.1 mm to about 50 mm by a predetermined method during or after the reaction depending on the need. Subsequently, in order to achieve more efficient foaming, the hydrogel containing cells is dried. It is possible to perform foaming by the blowing agent during drying instead of during reaction.

The drying temperature is not particularly limited., but is within a range of, for example, preferably from 100° C. to 300° C., more preferably from 120° C. to 220° C. in order to perform more efficient foaming. Similarly, the drying time is not particularly limited, but is preferably between 10 seconds and 3 hours. The hydrogel containing cells may be neutralized or may be chopped into smaller pieces prior to drying.

The drying method is not particularly limited. Drying may be performed by various methods, for example, heat drying, hot-air drying, vacuum drying, infrared drying, microwave drying, drum dryer drying, dehydrating by forming an azeotrope with a hydrophobic organic solvent, and high-humidity drying using high-temperature water vapor. Among these drying methods, hot-air drying and microwave drying are more preferred. In particular, the microwave drying is preferred. When the hydrogel containing cells is irradiated with a microwave, the cells swell into size several times or several tens times larger than the size before irradiated, thereby producing a water-absorbent resin having further improved absorption rate.

When microwave-drying the hydrogel containing cells, it is desirable to arrange the chopped hydrogel containing cells to have a thickness of preferably not less than 3 mm, more preferably not less than 5 mm, most preferably not less than 10 mm. In addition, when microwave-drying the hydrogel containing cells, it is particularly desirable to shape the hydrogel containing cells into a sheet having the above-mentioned thickness.

The water-absorbent resin of the present invention can be easily obtained at inexpensive costs by the above-mentioned polymerization, i.e., the above-mentioned production process. The water-absorbent resin is a porous cross-linking polymer having holes formed uniformly throughout the water-absorbent resin. The molar weight is relatively large, and the average pore diameter is within a range of preferably from 10 $\mu$m to 500 $\mu$m, more preferably from 20 $\mu$m to 400 $\mu$m, still more preferably from 30 $\mu$m to 300 $\mu$m, most preferably from 50 $\mu$m to 200 $\mu$m. The sheet-like water-absorbent resin obtained by microwave-drying the hydrogel containing cells has a bulk specific gravity within a range of from 0.01 g/cm$^3$ to 0.5 g/cm$^3$.

The average pore diameter is obtained by an image analysis of the profile of the dried water-absorbent resin with an electron microscope. More specifically, a histogram indicating the distribution of pore diameters of the water-absorbent resin is prepared by performing the image analysis, and the average pore diameter is obtained by calculating the number average of the pore diameters from the histogram.

Since the water-absorbent resin is porous having the above-mentioned average pore diameter, a sufficient liquid guide space which is necessary for an aqueous fluid to move into the water-absorbent resin is ensured under no pressure and under pressure conditions. Thus, the water-absorbent resin achieves excellent permeability and improved dispersion of the aqueous fluid, and increases the absorption rate and water retention capacity by capillarity. Moreover, since the water-absorbent resin is porous, even if the water-absorbent resin is in the form of particles, it is possible to retain the liquid permeability between the particles, thereby preventing a so-called gel blocking phenomenon. An average pore diameter smaller than 10 $\mu$m is not preferred because the liquid permeability and dispersibility in the aqueous solution is declined. Al average pore diameter larger than 500 $\mu$m is not preferred because the absorption rate is lowered.

The form and size (particle diameter) of the water-absorbent resin is not particularly limited, and can be suitably set according to the use of the water-absorbent resin. For example, the water-absorbent resin may be shaped into various forms, such as a sheet and a block. However, when using the water-absorbent resin as a sanitary material, it is desirable to perform grinding and classifying processes so as to arrange the average particle diameter within a range, preferably between 50 $\mu$m and 1,000 $\mu$m, more preferably between 150 $\mu$m and 800 $\mu$m, most preferably between 200 $\mu$m and 600 $\mu$m. It is also possible to form the water-absorbent resin into particles by granulation.

The water-absorbent resin with the above-mentioned structure may be treated with a surface cross-linking agent to form a covalent bond (secondary cross-linkages) and further increase the cross-link density in the vicinity of the surface. The surface cross-linking agent is not particularly limited as long as it is a compound having a plurality of functional groups capable of reacting with a carboxyl group of the water-absorbent resin to form a covalent band. By treating the water-absorbent resin with the surface cross-linking agent, the liquid permeability, the absorption rate of the water-absorbent resin, and the absorbent capacity and liquid permeability under pressure (to be described later) are further improved.

The surface cross-linking agent is not particularly limited, and preferred examples include:

polyhydric alcohol compounds, such as ethylene glycol, diethylene glycol, triethylene glycol, tetraethylene glycol, polyethylene glycol, propylene glycol, 1,3-propanediol, dipropylene glycol, 2,2,4-trimethyl-1,3-pentanediol, polypropylene glycol, glycerin, polyglycerin, 2-butene-1,4-diol, 1,4-butanediol, 1,5-pentanediol, 1,6-hexanediol, 1,2-cyclohexanedimethanol, 1,2-cyclohexanediol, trimethylolpropane, diethanolamine, triethanolamine, polyoxypropylene, oxyethylene-oxypropylene block copolymer, pentaerythritol, and sorbitol;

epoxy compounds, such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, and glycidol;

polyamine compounds, such as ethylenediamine, diethylenetriamine, triethylenetetramine, tetraethylenepentamine, pentaethylenehexamine, polyethylene-imine, and polyamide-polyamine;

haloepoxy compounds, such as epichlorohydrin, epibromohydrin, and α-methylepichlorohydrin;

condensation products of the above-mentioned polyamine compounds and haloepoxy compounds;

polyisocyanate compounds, such as 2,4-trilene diisocyanate, and hexamethylene diisocyanate;

polyoxazoline compounds, such as 1,2-ethylenebisoxazoline;

silane coupling agents, such as γ-glycidoxypropyltrimetoxysilane, and γ-aminopropyltrimetoxysilane; and alkylene carbonate compounds, such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxane-2-one, 4-methyl-1,3-dioxane-2-one, 4,6-. dimethyl-1,3-dioxane-2-one, and 1,3-dioxopan-2-one. Among the exemplified surface cross-linking agents, the polyhydric alcohol compounds, epoxy compounds, polyamine compounds, condensation products of the polyamine compounds and haloepoxy compounds, and alkylene carbonate compounds are more preferred.

These surface cross-linking agents may be used individually, or in combination. When using more than ones type of surface cross-linking agents, it is possible to obtain a water-absorbent resin having further improved absorbent characteristics by using a combination of a first surface cross-linking agent and a second surface cross-linking agent having different solubility parameters (SP values). The solubility parameter is a value which is generally used as a factor representing the polarity of a compound.

The first surface cross-linking agent is a compound which is reactive with the carboxyl group of the water-absorbent resin and has a solubility parameter of not lower than 12.5 $(cal/cm^3)^{1/2}$, for example, glycerin. The second surface cross-linking agent is a compound which is reactive with the carboxyl group of the water-absorbent resin and has a solubility parameter less than 12.5 $(cal/cm^3)^{1/2}$, for example, ethylene glycol diglycidyl ether.

The amount of the surface cross-linking agent with respect to the water-absorbent resin varies depending on the combination of water-absorbent resin and surface cross-linking agent. However, the amount of the surface cross-linking agent to be used is within a range of preferably from 0.01 weight parts to 5 weight parts, more preferably from 0.05 weight parts to 3 weight parts, based on 100 parts by weight of the dry water-absorbent resin. By using the surface cross-linking agent in an amount within the above-mentioned range, it is possible to further improve the water absorption characteristics with respect to body fluids (aqueous fluids), such as urine, sweat, and blood. If the amount of the surface cross-linking agent is less than 0.01 weight parts, the cross-link density in the vicinity of the surface of the water-absorbent resin can hardly be increased. On the other hand, if the amount of the surface cross-linking agent exceeds 5 weight parts, the surface cross-linking agent becomes excessive, causing uneconomical results and difficulty in controlling the cross-link density to be a suitable value.

The method of treating the water-absorbent resin with the surface cross-linking agent is not particularly limited. For example, the following three methods are listed. ① A method including mixing the water-absorbent resin and the surface cross-linking agent without the presence of solvent. ② A method including dispersing the water-absorbent resin in a hydrophobic solvent such as cyclohexane and pentane, and mixing the surface cross-linking agent and the water-absorbent resin. ③ A method including dispersing or dissolving the surface cross-linking agent in a hydrophilic solvent, and spraying or dropping the solution or the dispersion into the water-absorbent resin to mix them. Among these methods, ③ is most preferred. Water, or a mixture of water and an organic solvent soluble in water is suitably used as the hydrophilic solvent.

Examples of the organic solvent include:
lower alcohols, such as methyl alcohol, ethyl alcohol, n-propyl alcohol, isopropyl alcohol, n-butyl alcohol, isobutyl alcohol, an d t-butyl alcohol;
ketones, such as acetone;
ethers, such as dioxane, ethyleneoxide (EO) added compound of monohydric alcohol, and tetrahydrofuran;
amides, such as N,N-dimethylformamide, and ε-caprolactam; and
sulfoxides, such as dimethyl sulfoxide. These organic solvents may be used individually, or in combination.

The amount of the hydrophilic solvent with respect to the water-absorbent resin and the surface cross-linking agent varies depending on the combination of water-absorbent resin, surface cross-linking agent and hydrophilic solvent. However, the amount of hydrophilic solvent to be used is preferably not higher than 200 weight parts, more preferably within a range of from 0.01 weight parts to 50 weight parts, still more preferably from 0.1 weight parts to 50 weight parts, most preferably from 0.5 weight parts to 20 weight parts, based on 100 parts by weight of the water-absorbent resin.

A mixer for use in mixing the water-absorbent resin and the surface cross-linking agent preferably has a great mixing power so as to mix them evenly and surely. Preferred examples of the mixer are a cylindrical mixer, double-wall conical mixer, high-speed agitation-type mixer, V-shaped mixer, ribbon blender, screw mixer, fluid oven rotary desk mixer, airborne mixer, double-arm kneader, internal mixer, crush-type kneader, rotary mixer, and screw extruder.

The treatment temperature and treatment time when treating the water-absorbent resin with a surface cross-linking agent are not particularly limited, and are set according to the combination of water-absorbent resin and surface cross-linking agent, and a desired cross-link density. However, a preferred treatment temperature is, for example, within a range of from 0° C. to 250° C.

When treating the water-absorbent resin with a surface cross-linking agent, it is possible to further add a mixing assistant, if necessary. As the mixing assistant, powder of fine particles which are insoluble in water, surface active agents, organic acids, inorganic acids, and polyamino-acids are listed. Examples of organic acids are saturated carboxylic acids, such as citric acid, lactic acid, and succinic acid. As the inorganic acids, for example, phosphoric acid, sulfuric acid, and hydrochloric acid are given. These mixing assistants may be used individually, or in combination. The mixing assistant is preferably used in an amount ranging from 0.01 weight parts to 5 weight parts based on 100 parts by weight of the water-absorbent resin. The method for mixing the water-absorbent resin, the surface cross-linking agent and the mixing assistant is not particularly limited.

The water-absorbent resin whose cross-link density in the vicinity of the surface is improved by the formation of a covalent bond, i.e., the water-absorbent resin to which the above-mentioned treatment has been applied, may have further improved cross-link density in the vicinity of the surface by treating it with a cationic compound to form an ionic bond (secondary cross linkage). The cationic compound is not particularly limited as along as it is a compound capable of forming an ionic bond by reacting with the carboxylic group of the water-absorbent resin (i.e., the carboxylic group which has not reacted with the surface cross-linking agent). By treating the water-absorbent resin -with the cationic compound, it is possible to further improve the water absorption characteristics, such as the absorption rate, dispersion, water retention capacity, dry touch, and absorbent capacity under pressure.

Examples of the cationic compound are:
low-molecular-weight polyamine compounds, such as ethylenediamine, diethylenetriamine, triethylenetetramine, tetraethylenepentamine, and pentaethylenehexamine;
cationic polyelectrolytes, such as polyethylene-imine, modified polyethylene-imine modified to be water-soluble by epihalohydrin, polyamine, polyamide-amine modified by grafting ethylene-imine, protonated polyamide-amine, polyetheramine, polyvinylamine, polyalkylamine, polyvinylimidazole, polyvinylpyridine, polyvinylimidazoline, polyvinyl tetrahydropyridine, polydialkylamino alkylvinyl ether, polydialkylamino alkyl (meth) acrylate, and polyallylamine, and salts thereof; and polyvalent metal compounds, such as hydroxides, chlorides, sulfate, and carbonate of polyvalent metals including zinc, calcium, magnesium, aluminum, iron and zirconium. However, the cationic compound is not necessarily limited to those mentioned above. These cationic compounds may be used individually, or in combination. Among the exemplified cationic compounds, the cationic polyelectrolytes and salts thereof are more preferred.

The amount of the cationic compound with respect to the water-absorbent resin varies depending on the combination of water-absorbent resin and cationic compound. However, the cationic compound is used in an amount ranging preferably from 0.01 weight parts to 5 weight parts, more preferably from 0.1 weight parts to 3 weight parts, based on 100 parts by weight of the dried water-absorbent resin. By using the cationic compound in an amount within the above-mentioned range, it is possible to obtain a water-absorbent resin having further improved water absorption characteristics, such as the absorption rate, dispersion, water retention capacity, dry touch, and absorbent capacity under pressure. The method of treating the water-absorbent resin with the cationic compound is the same as that used for treating the water-absorbent resin with the surface cross-linking agent. The treatment temperature and treatment time are not particularly limited, and are set according to the combination of water-absorbent resin and cationic compound, and a desired cross-link density. However, a preferred treatment temperature is, for example, room temperature, and may be increased to temperatures ranging from 50° C. to 100° C., if necessary.

By the above-mentioned method, it is possible to easily and industrially produce the water-absorbent resin at an inexpensive cost. The resulting water-absorbent resin is porous having an average pore diameter within a range of from 10 $\mu$m to 500 $\mu$m. The amount of water absorbed by the water-absorbent resin 60 minutes after the initiation of absorbent capacity under pressure is preferably no lower than 25 g/g, more preferably no lower than 30 g/g. The water-soluble component content in the water-absorbent resin is preferably no higher than 15 weight percent, more preferably within a range of from 1 weight percent to 10 weight percent. Moreover, the residual monomer content in the water-absorbent resin is preferably no higher than 500 ppm, more preferably no higher than 300 ppm, and most preferably no higher than 100 ppm. Since the physical properties of the water-absorbent resin are superior and balanced, the water absorption characteristics of the water-absorbent resin, such as the liquid permeability under pressure, are excellent.

Furthermore, it is possible to impart various functions to the water-absorbent resin by adding thereto deodorant, perfume, various inorganic powders, blowing agent, pigment, dye, hydrophilic short fiber, plasticizer, thickening agent, surface-active agent, fertilizer, oxidizer, reducing agent, water and salts, if necessary.

A water-absorbent resin composition of the present invention is obtained by mixing inorganic powder in the form of fine particles and the above-mentioned water-absorbent resin, i.e., the water-absorbent resin particles whose average particle diameter is arranged within a range of preferably from 50 $\mu$m to 1,000 $\mu$m, more preferably from 150 $\mu$m to 800 $\mu$m, most preferably from 200 $\mu$m to 600 $\mu$m, through the gliding and classifying steps. The water-absorbent resin composition preferably contains a water-absorbent resin formed by an unsaturated monomer containing an acrylate monomer as a chief constituent.

As the inorganic powder, inactive substances which are inactive with respect to the aqueous fluid and the like, for example, fine particles of various inorganic compounds and fine particles of clay mineral are used. Preferred inorganic compounds have suitable affinity with respect to water, and insoluble or slightly-soluble in water. Examples of such inorganic compounds are metal oxides, such as silicon dioxide and titanium oxide, silicic acid (salt) such as natural zeolite and synthetic zeolite, kaolin, talc, clay, and bentonite. Silicon dioxide and silicic acid (salt) are more preferred. In particular, silicon dioxide and silicic acid (salt) whose average particle diameter is not larger than 200 $\mu$m when measured by a Coulter Counter are most preferred.

The amount of inorganic powder to be used varies depending on the combination of water-absorbent resin and inorganic power. The inorganic powder is used in an amount ranging preferably from 0.001 weight parts to 10 weight parts, more preferably from 0.01 weight parts to 5 weight parts, based on 100 parts by weight of the water-absorbent resin. The method of mixing the water-absorbent resin and inorganic powder is not particularly limited. For example, a dry blending method or a wet blending is used. In particular, dry blending is preferred.

Regarding a water-absorbent resin composition of the above-mentioned structure, the water retention capacity is not lower than 20 g/g, the absorption rate is not higher than 120 seconds, and the liquid permeability is not higher than 200 seconds. The water-absorbent resin composition is made into an absorbent article by, for example, being composite (combined) with fibrous material such as pulp.

The absorbent article is not particularly limited, and examples includes: sanitary materials (body fluids absorbent articles) such as paper diapers, sanitary napkins, incontinence pads, wound protecting material and wound healing material; absorbent articles for absorbing urine of pets; materials of construction and building, such as building material, water retentive material for soil, packing material, and gel pusule; materials for food, such as drip absorbing material, freshness retentive material, and heat insulating material; various industrial articles, such as oil and water separating material, condensation preventing material, and coagulant; and agricultural and horticultural articles, such as water retentive material for plant and soil. For instance, paper diaper is formed by layering a back sheet (back material) made of waterproof material, the above-mentioned water-absorbent resin composition, and a top sheet (front material) made of a liquid permeable material in this order, fix these materials to each other, and fastening a gather (an elastic section) and a so-called tape fastener onto the laminate. The paper diaper includes paper-diaper-containing training pants which are used for teaching a young child when to use the toilet.

The water-absorbent resin composition has sufficient fluid passing space necessary for the movement of an aqueous fluid into the water-absorbent resin under pressure even in a so-called high dense condition, i.e., even when the proportion of the water-absorbent resin composition to the total amount of the water-absorbent resin composition and the fibrous material is not lower than 50 weight percent. Thus, the water-absorbent resin composition can achieve excellent permeability and dispersion of the aqueous fluid under pressure, and can improve the absorption rate and water retention capacity by capillarity without causing a gel blocking phenomenon. Consequently, even in the use in which the aqueous fluid is required to be absorbed a plurality of times, for example, when the absorbent article is a sanitary material, it is possible to prevent the sanitary material from leakage. Moreover, a reduction in the thickness of the sanitary material can be achieved.

For a fuller understanding of the nature and advantages of the invention, reference should be made to the ensuing detailed description taken in conjunction with the accompanying drawings.

BEST MODE FOR CARRYING OUT THE INVENTION

Figure 1:
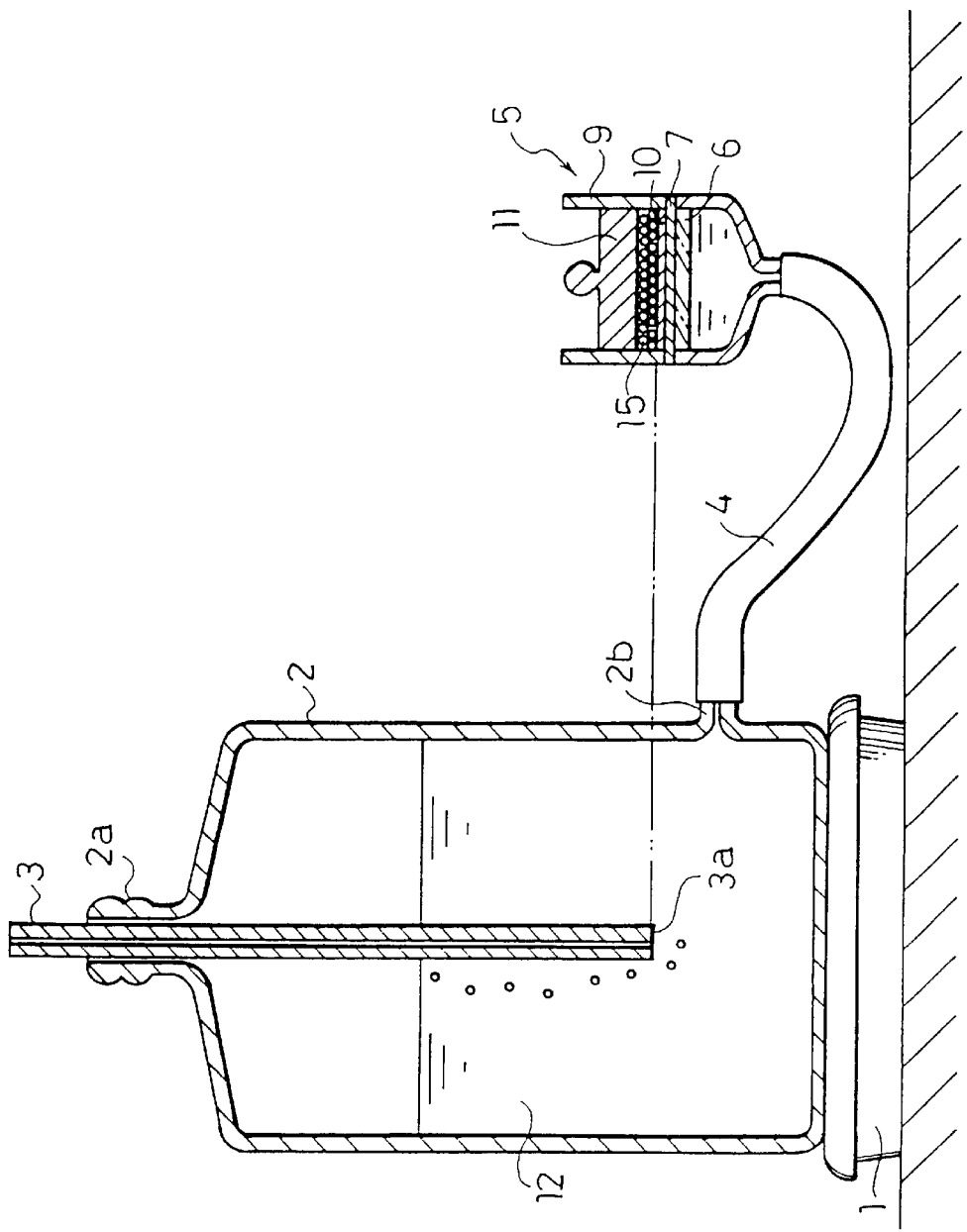
FIG. 1 is a schematic cross sectional view of a measurement device used for measuring the absorbent capacity under pressure that is one of the performances exhibited by a water-absorbent resin of the present invention.

The following examples and comparative examples are provided to describe the present invention in greater detail, and are not meant to limit the present invention. Unless otherwise specified, "part" and "percent" as used in the following descriptions refer to "weight part" and "weight percent", respectively.

The performances of a water-absorbent resin or a water-absorbent resin composition were measured by the following methods. When measuring the performances, a water-absorbent resin in particle form was used. More specifically, the particle distribution of the water-absorbent resin was adjusted so that particles having particle diameters ranging from 850 μm to 500 μm are 25 percent to 35 percent, particles having a particle diameters ranging rom 500 μm to 150 μm are 65 percent to 75 percent, and particles having a particle diameters ranging from 150 μm to 10 μm are 0 percent to 10 percent when the total amount is 100 percent.

In addition, a method for producing 2,2'-azobis(2-methyl propionamidine)dicarylate as an acrylic acid salt (blowing agent) of an azo-compound containing an amino group represented by general formula (1) above will be discussed below.

(1) Water Retention Capacity of Water-absorbent Resin 0.2 grams of water-absorbent resin was evenly placed in a tea bag (6 cm×6 cm), and the tea bag was sealed by heat.

The tea bag was then placed in an aqueous 0.9 percent sodium chloride solution (physiologic saline). The tea bag was removed from the aqueous solution 60 minutes later, and centrifuged at 1,300 rpm for three minutes using a centrifugal separator. The weight $W_{1a}$ (g) of the tea bag was measured. The same test was performed using an empty bag containing no water-absorbent resin, and the weight $W_{0a}$ (g) of the empty bag was measured. The water retention capacity (gig) was calculated from the weights $W_{1a}$ and $W_{0a}$ according to the following equation.

Water retention capacity(g/g)

=($W_{1a}$ (g)–W($W_{0a}$(g))/water-absorbent resin weight (g)

(2) Residual Monomer Content in Water-absorbent Resin

After placing 100 ml of deionized water in a 200 ml beaker, the deionized water was completely gelated by adding 1.0 gram of water-absorbent resin while agitating. One hour later, 5 ml of aqueous phosphoric acid solution was added to the resulting gel to condensate the gel. The condensed gel was filtered with a filter paper while agitating, and the filtrate, i.e., water produced by condensation, was analyzed using a high-speed liquid chromatography.

Similarly, an aqueous monomer solution with a known concentration was analyzed as a standard solution to obtain a calibration curve. By setting the calibration curve as an external standard, the residual monomer content (ppm) of the water-absorbent resin was calculated while considering the dilution of the filtrate. Here, the residual monomer content is given by a reduced value corresponding to the solid component in the water-absorbent resin.

(3) Water-soluble Component Content in

Water-Absorbent Resin 0.5 grams of water-absorbent resin was dispersed in 1,000 ml of deionized water, agitated for 16 hours, and filtered with a filter paper. The amount (percent) of water-soluble component was obtained by colloid-titrating the resulting filtrate.

(4) Dispersion Rate (Dispersibility) of

Water-absorbent Resin

Various reagents were first dissolved in water to prepare aqueous solutions containing 600 ppm to 700 ppm sodium cation, 65 ppm to 75 ppm calcium cation, 55 ppm to 65 ppm magnesium cation, 1,100 ppm to 1,200 ppm potassium cation, 240 ppm to 280 ppm phosphorus, 450 ppm to 500 ppm sulfur, 1,100 ppm to 1,300 ppm chlorine, and 1,300 ppm to 1,400 ppm sulfate group, respectively. These aqueous solutions were used as synthetic urine.

Next, 1.0 gram of water-absorbent resin was evenly spread in a Petri dish with an internal diameter of 58 mm and a depth of 12 mm. Subsequently, 20 grams of synthetic urine having a temperature of 25° C. was calmly pored into the center of the Petri dish at a time. The time taken from the initiation of pouring of synthetic urine to the time at which absorption of all the synthetic urine by the water-absorbent resin was confirmed by eyes, was measured. The measured time was taken as a dispersion rate (seconds).

(5) Dry Touch of Water-absorbent Resin 20 pieces of filter paper with a diameter of 55 mm were layered on the water-absorbent resin after measuring the dispersion rate, i.e., on the water-absorbent resin which absorbed the synthetic urine and swelled. The weight of the filter paper was measured in advance. A 500-gram weight (load) was placed on the filter paper, and the filter paper was left for one minute. The dry touch was evaluated by measuring the weight of the filter paper after the one minute leave and calculating an increase (g) in the weight. Namely, as the amount of synthetic urine moved from the swelled water-absorbent resin to the filter paper becomes smaller, the increase in the weight of the filter paper is smaller. Moreover, as the increase in the weight is smaller, the touch of the swelled water-absorbent resin becomes drier. Namely, it can be evaluated that the dry touch of the water-absorbent resin is excellent.

(6) Absorbent Capacity of Water-absorbent

Resin under Pressure

A measuring device for use in measuring the absorbent capacity under pressure is first explained briefly with reference to FIG. 1.

As illustrated in FIG. 1, the measuring device includes a scale 1, a container 2 of a predetermined capacity placed on the scale 1, an outside air inlet pipe 2, a tube 4 made of a silicone resin, a glass filter 6, and a measuring section 5 placed on the glass filter 6. The container 2 has an opening section 2a at the top, and an opening 2b on the side section thereof. The outside air inlet pipe 3 was fitted into the opening section 2a, and the tube 4 was attached to the opening 2b. The container 2 contains a predetermined amount of synthetic urine 12. The bottom end of the outside air inlet pipe 3 sinks in the synthetic urine 12. The outside air inlet pipe 3 was provided to keep the pressure in the container 2 at substantially atmospheric pressure. The glass filter 6 was formed to have a diameter of 55 mm. The container 2 and the glass filter 6 are connected to each other with the tube 4. The position and height of the glass filter 6 with respect to the container 2 was fixed.

The measuring section 5 includes filter paper 7, a bearing cylinder 9, a metal gauge 10 attached to the bottom of the bearing cylinder 9, and a weight 11. In the measuring section 5, the paper filter 7 and the bearing cylinder 9 (i.e., the metal gauge 10) are placed in this order on the glass filter 6, and the weight 11 is placed inside the bearing cylinder 9, i.e., on the metal gauge 10. The metal gauge 10 was made of stainless steel and is 400 mesh (38 $\mu$m in mesh). A predetermined amount of water-absorbent resin 15 having a predetermined particle diameter was evenly spread over the metal gauge 10 in measuring. In addition, the top surface of the metal gauge 10, i.e., the contact surface between the metal gauge 10 and the water-absorbent resin 15, was arranged at the same level as the height of a lower end surface 3a of the outside air inlet pipe 3. The weight of the weight 11 was adjusted so that a load of 50 g/cm$^2$ was evenly applied to the metal gauge 10, i.e., to the water-absorbent resin 15.

The absorbent capacity under pressure was measured using a measuring device of the above-mentioned structure. The following description will discuss the measuring method.

First, prescribed preparations were made. For example, a predetermined amount of the synthetic urine 12 was placed in the container 2, and the outside air inlet pipe 3 was fitted into the container 2. Next, the filter paper 7 was placed on the glass filter 6. At the same time as placing the filter paler 7 on the glass filter 6, 0.9 grams of water-absorbent resin was evenly spread inside the bearing cylinder 9, i.e., on the metal gauge 10, and the weight 11 was then placed on the water-absorbent resin 15.

Subsequently, the metal gauge 10, i.e., the bearing cylinder 9 whereupon the water-absorbent resin 15 and the weight 11 were placed, was placed on the filter paper 7 so that the center of the bearing cylinder 9 coincides with the center of the glass filter 6.

Weight $W_2(g)$ of the synthetic urine 12 absorbed by the water-absorbent resin 15 was measured using the scale 1 with the passage of time over 60 minutes after the placement of the bearing cylinder 9 on the filter paper 7. The same process was performed without using the water-absorbent resin 15, and the weight, i.e., the weight of synthetic urine 12 absorbed by members other than the water-absorbent resin 15, for example, the filter paper 7, was measured as blank weight $W_3(g)$ with the scale 1. The absorbent capacity under pressure (g/g) was calculated from the weights $W_2$ and $W_3$ according to the following equation.

Absorbent capacity under pressure (g/g)

$=(W_2(g)-W_3(g))$/water-absorbent resin weight(g)

(7) Water Retention Capacity of

Water-absorbent Resin Composition 0.2 grams of water-absorbent resin composition was evenly placed in a tea bag (6 cm×6 cm), and the tea bag was sealed by heat. The tea bag was then placed in an aqueous 0.9 percent sodium chloride solution (physiologic saline). 60 minutes later, the tea bag was removed from the solution and centrifuged at 250G for three minutes using a centrifugal separator. The weight $W_{1b}$ (g) of the tea bag was measured. The same test was performed using an empty bag containing no water-absorbent resin composition, and the weight $W_{0b}$ (g) of the empty bag was measured. The water retention capacity (g/g) was calculated from the weights $W_{1b}$ and $W_{0b}$ according to the following equation. Water retention capacity(g/g)

$=(W_{1b}(g)-W_{0b}(g))$/water-absorbent resin composition weight (g)

(8) Absorption Rate of Water-absorbent

Resin Composition 1.0 gram of water-absorbent resin composition was placed in a polypropylene cylindrical cup having an internal diameter of 50 mm and a height of 70 mm. Subsequently, 28 grams of physiologic saline was pored into the cup. The time taken for reaching a state in which the physiologic saline was completely absorbed by the water-absorbent resin composition and become unseen from the initiation of pouring of the physiologic saline was measured. The measurement was performed three times, and the average value was taken as the absorption rate (seconds).

(9) Rate of Fluid to Flow through Water-absorbent Resin

Composition (Liquid Permeability) Under Pressure

A measuring device for use in measuring the liquid permeability under pressure will be briefly explained with reference to FIG. 2.

Figure 2:
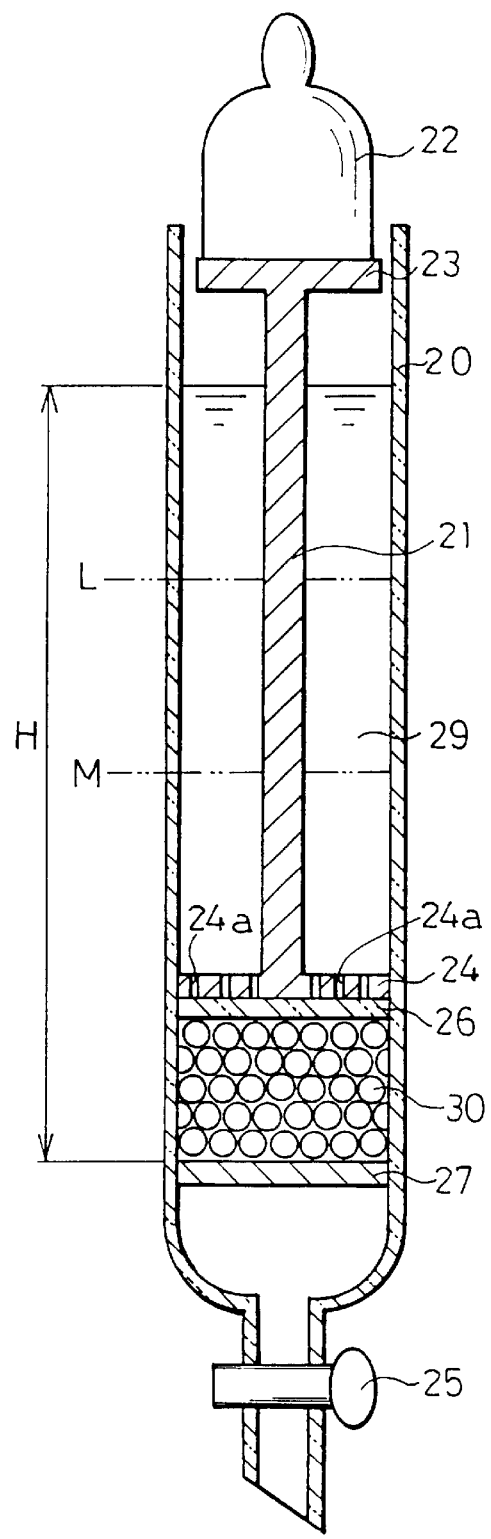
FIG. 2 is a schematic cross sectional view of a measurement device used for measuring the liquid permeability-that is one of the performances exhibited by a water-absorbent resin composition of the present invention.

As illustrated in FIG. 2, the measuring device includes a glass column 20, a pressure shaft 21, and a weight 22. The glass column 20 is formed into a cylindrical shape with an internal diameter of one inch and a height of 400 mm. Attached below the glass column 20 is a cock 25 which is freely opened and closed. Moreover, a glass filter 27 is inserted into the glass column 20 so as to fill the glass column 20 with a water-absorbent resin composition 30. The mesh of the glass filter 27 is #G2. The glass column 20 is provided with standard lines L and M. The standard line L is given at a level 150 mm distant from the top surface of the glass filter 27. The standard line M is given at a level 100 mm distant from the top surface of the glass filter 27. The glass column 20 contains a predetermined amount of physiologic saline 29 therein. BIO-COLUMN CF-30K (trade name, catalog code: 22-635-07, produced by Kabushiki Kaisha Iuchi Seieido) was used as the glass column 20.

A plate 23 on which the weight 22 is placable is fixed to the upper end section of the pressure shaft 21. The plate 23 is shaped into a circular plate of a diameter slightly smaller than the internal diameter of the glass column 20. The pressure shaft 21 has a length that prevents the plate 23 from sinking in the physiologic saline 29.

Moreover, a pressure plate 24 is fixed to the lower end section of the pressure shaft 21. The pressure plate 24 is shaped into a circular plate with a diameter of about 1 inch and a thickness of 10 mm, and has 64 holes 24a on the upper surface through the lower surface. The holes 24a have a diameter of 1 mm and positioned at an interval of about 2 mm. In this structure, the physiologic saline 29 flows from the upper surface to the lower surface of the pressure plate 24 through the holes 24a.

The pressure shaft 21, i.e., the pressure plate 24, is movable in upward and downward directions in the glass column 20. A glass filter 26 is attached to the lower surface of the pressure plate 24. The mesh of the glass filter 26 is #G0.

The weight of the weight 22 is adjusted so as to allow a load of 24.5 g/cm$^2$ to be evenly applied to the swelled water-absorbent resin composition 30.

The liquid permeability was measured with a measuring device having the above-mentioned structure. The measuring method will be discussed below.

First, the cock 25 is closed, and the glass filter 27 is inserted into the glass column 20. 0.5 grams of water-absorbent resin composition is then placed in the glass column 20. Next, an amount of the physiologic saline 29 that could not be absorbed by the water-absorbent resin composition 30, i.e., an excessive amount of physiologic saline 29, is placed in the glass column 20 to swell the water-absorbent resin composition 30.

About one hour later, the water-absorbent resin composition 30 sufficiently settles out and the swelling thereof reaches an equilibrium condition. Then, the pressure shaft 21 is inserted into the glass column 20. More specifically, the pressure plate 24 is placed on the water-absorbent resin composition 30 while discharging the air so that the air does not remain between the swelled water-absorbent resin composition 30 and the glass filter 26. Thereafter, the weight 22 is placed on the plate 23 to press the water-absorbent resin composition 30.

Subsequently, the physiologic saline 29 is added to adjust the height (fluid depth) H from the upper surface of the glass filter 27 (the lowest section of the water-absorbent resin composition 30) to the liquid level to be 200 mm.

Next, the cock 25 is opened to discharge the physiologic saline 29, and the time between a passage of the liquid level of the physiologic saline 29 through the standard line L and a passage of the liquid level through the standard line M is measured. The amount of the physiologic saline 29 discharged during the measured time is about 25 ml (observed value).

The measurement is performed three times, and the average value is taken as the rate of fluid to flow "liquid permeability" (seconds). The measurement is also carried out in the same manner without using the water-absorbent resin composition 30. In this case, the liquid permeability was 10 seconds.

(10) Method for Producing 2,2'-azobis(2-methyl propionamidine)diacrylate 6.7 parts aqueous 37 percent sodium acrylate solution as acrylic acid salt was added to 36 parts aqueous 10 percent 2,2'-azobis(2-methyl propionamidine)dihydrochloride solution as a blowing agent precursor which was kept at 20 °C. while agitating the aqueous 2,2'-azobis(2-methyl propionamidine)dihuydrochloride solution at 1,200 rpm. Several seconds after the addition, the aqueous solution appeared cloudy or white, and white fine solid particles with an average particle diameter of 10 μm were generated. The fine solid particles were evenly dispersed in the aqueous solution.

About 2.2 parts fine solid particles were isolated by filtering the aqueous solution, and then purified by washing with water. The ultraviolet absorption spectrum (UV) of the resulting fine solid particles was measured. As a result, absorption unique to azo groups was observed at 365 nm. Additionally, elemental analysis of the fine solid particles was performed, and $^1$H-NMR (nuclear magnetic resonance) and infrared absorption spectrum (IR) were measured. In the measurement of $^1$H-NMR, heavy water was used as a solvent.

Figure 3:
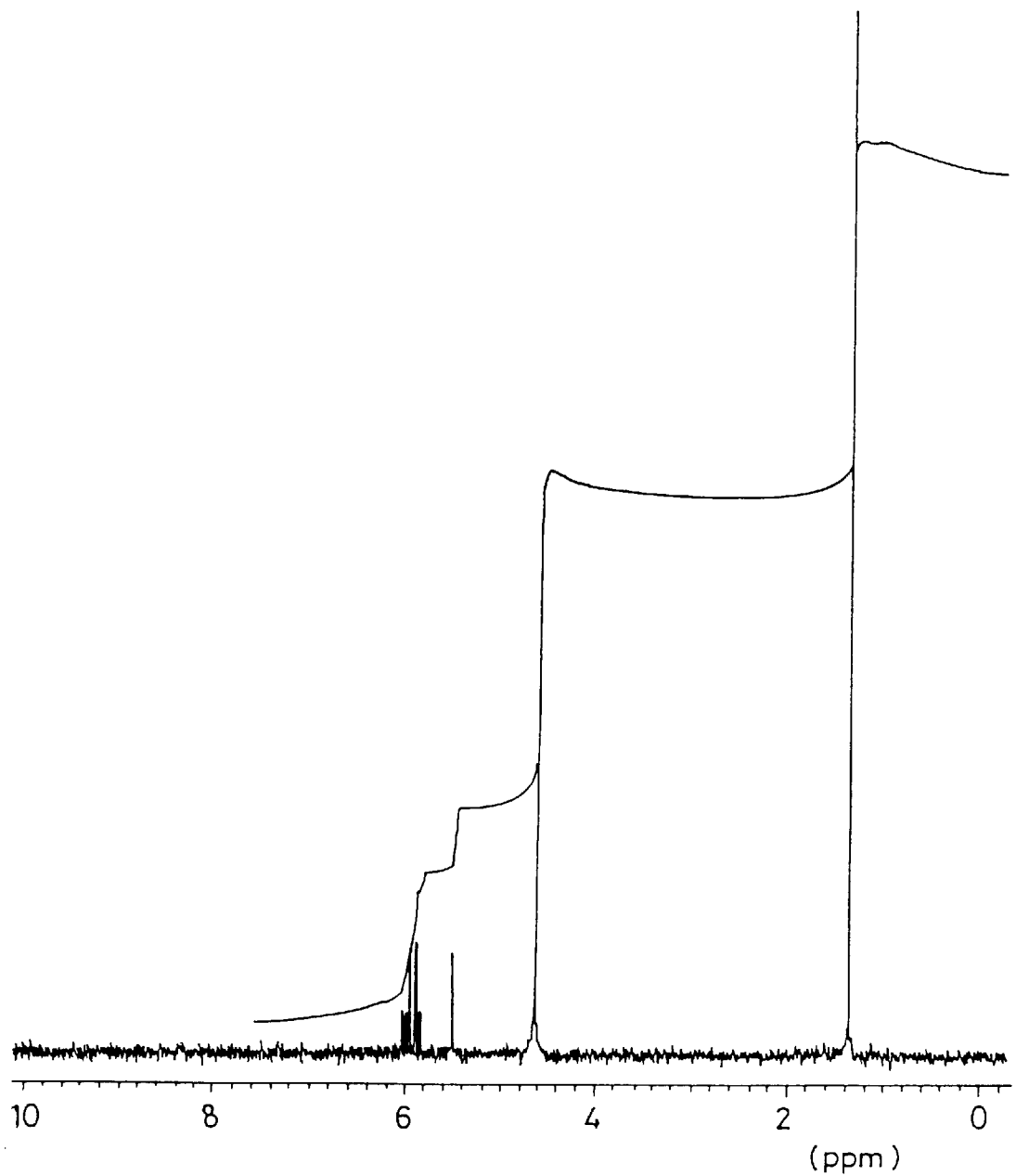
FIG. 3 is a chart of $^1$H-NMR of 2,2'-azobis(2-methyl propionamidine)dicarylate as a blowing agent of the present invention.
Figure 4:
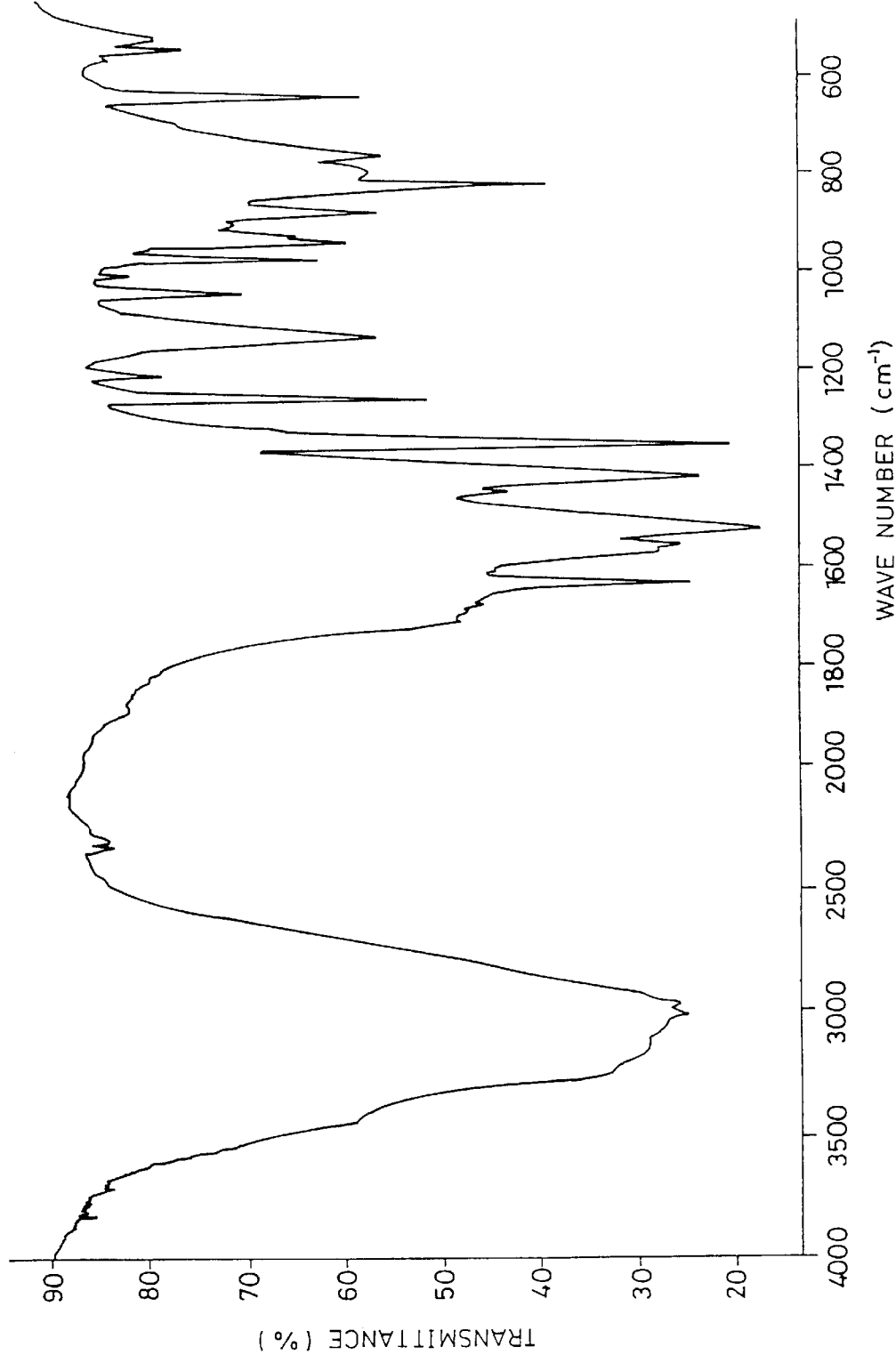
FIG. 4 is a chart of infrared absorption spectrum (IR) of the 2,2'-azobis (2-methyl propionamidine) dicarylate.

As a result, it was confirmed that the fine solid particles were 2,2'-azobis(2-methyl propionamidine)diacrylate as an acrylic acid salt of an azo-compound containing an amino group (blowing agent), represented by general formula (1) mentioned above. The chart of $^1$H-NMR and the chart of IR are shown in FIGS. 3 and 4, respectively.

EXAMPLE 1

First, 38.6 parts acrylic acid as unsaturated monomer, 409 parts aqueous 37 percent sodium acrylate solution, 0.48 parts trimethylolpropane triacrylate as a cross-linking agent, and 53 parts deionized water were mixed to prepare an aqueous monomer solution. Namely, the aqueous monomer solution is an aqueous 38 percent acrylate monomer solution with a neutralization rate of 75 mole percent.

By bubbling a nitrogen gas into the aqueous monomer solution while keeping the temperature of the aqueous monomer solution at 25° C., dissolved oxygen was removed. Next, 4.3 parts 10 percent aqueous 2,2'-azobis(2-methyl propionamidine)dihydrochloride solution as a blowing agent precursor was added while agitating the aqueous monomer solution. Thereafter, the aqueous solution was agitated at 25° C. under the flow of nitrogen.

About seven minutes after the initiation of agitation, the aqueous solution appeared cloudy or white, and white fine solid particles with an average particle diameter of 9 μm were generated. The fine solid particles was 2,2'-azobis(2-methyl propionamidine)diacrylate as a blowing agent. Moreover, 10 minutes after the initiation of agitation, the solid content in the aqueous monomer solution, i.e., the amount of 2,2'-azobis(2-methyl propionamidine)diacrylate generated became 0.29 percent based on the acrylate monomer. The 2,2'-azobis(2-methyl propionamidine)diacrylate was uniformly dispersed in the aqueous monomer solution.

At this time (10 minutes after the initiation of agitation), 2.6 parts aqueous 10 percent sodium persulfate solution and 1 part aqueous 1 percent L-ascorbic acid solution were added as a redox initiator (radical polymerization initiator) while agitating the aqueous monomer solution. After sufficiently agitating the aqueous monomer solution, it was left at rest.

About 10 minutes after the addition of aqueous sodium persulfate solution, the temperature of the aqueous monomer solution reached about 89° C. Thereafter, the aqueous monomer solution was left at rest for further 10 minutes while keeping the temperature thereof between 70° C. and 80° C. to polymerize the acrylate monomer. As a result, a hydrogel having cells as a porous cross-linking polymer was obtained.

The resulting hydrogel having cells was removed, made into small pieces of a size ranging from about 20 mm to 1 mm, and hot-air dried at 150° C. with a hot-air drier. Subsequently, the dried pieces were ground with a roll mill, and sieved using a standard screen (850 μm) according to JIS standards, thereby producing a water-absorbent resin of the present invention.

It was confirmed through an electron photomicrograph that the above-mentioned water-absorbent resin was porous. The average pore diameter of the water-absorbent resin was 60 μm. Moreover, various physical properties of the water-absorbent resin were measured by the above-mentioned methods. The water retention capacity was 29 g/g, the residual monomer content was 200 ppm, the water-soluble component content was 9 percent, the dispersion rate was 33 seconds, the dry touch was 4.3 g, and the absorbent capacity under pressure was 11 g/g. The results are shown in Table 1.

EXAMPLE 2

First, 38.6 parts acrylic acid, 409 parts aqueous 37 percent sodium acrylate solution, 1.08 parts polyethylene glycol diacrylate as a cross-linking agent, and 53 parts deionized water were mixed to prepare an aqueous monomer solution. Namely, the aqueous monomer solution is an aqueous 38 percent acrylate monomer solution with a neutralization rate of 75 mole percent.

By bubbling a nitrogen gas into the aqueous monomer solution while keeping the temperature of the aqueous monomer solution at 25° C., dissolved oxygen was removed. Next, 4.3 parts aqueous 10 percent 2,2'-azobis(2-methyl propionamidine)dihydrochloride solution was added while agitating the aqueous monomer solution. Thereafter, the aqueous solution was agitated at 25° C. under the flow of nitrogen.

About seven minutes later from the initiation of agitation, the aqueous solution appeared cloudy or white, and 2,2'-azobis(2-methyl propionamidine)diacrylate in the form of white fine particles with an average particle diameter of 9 μm was generated. 10 minutes later from the initiation of agitation, the amount of 2,2'-azobis (2-methyl propionamidine)diacrylate generated became 0.29 percent based on the acrylate monomer. The 2,2'-azobis(2-methyl propionamidine)diacrylate was evenly dispersed in the aqueous monomer solution.

At this time, 2.6 parts aqueous 10 percent sodium persulfate solution and 1 part aqueous 1 percent L-ascorbic acid solution were added while agitating the aqueous monomer solution. After the addition, the aqueous monomer solution continued to be agitated.

About 10 minutes after the addition of aqueous sodium persulfate solution, the temperature of the aqueous monomer solution reached about 79° C. Thereafter, the aqueous monomer solution was further agitated for 10 minutes while keeping the temperature thereof between 70° C. and 80° C. to polymerize the acrylate monomer. As a result, a hydrogel having cells was obtained.

The resulting hydrogel having cells was removed, and the same operations as in Example 1 were performed to produce a water-absorbent resin. The average pore diameter of the water-absorbent resin was 70 μm. Moreover, various physical properties of the water-absorbent resin were measured by the above-mentioned methods. The water retention capacity was 33 g/g, the residual monomer content was 170 ppm, the water-soluble component content was 6 percent, the dispersion rate was 30 seconds, the dry touch was 3.9 g, and the absorbent capacity under pressure was 12 g/g. The results are shown in Table 1.

EXAMPLE 3

An aqueous monomer solution was prepared in the same manner as in Example 2. By bubbling a nitrogen gas into the aqueous monomer solution while keeping the temperature of the aqueous monomer solution at 25° C., dissolved oxygen was removed. Next, 21 parts aqueous 10 percent 2,2'-azobis(2-methyl propionamidine) dihydrochloride solution was added while agitating the aqueous monomer solution. Thereafter, the aqueous solution was agitated at 25° C. under the flow of nitrogen.

About one minute later from the initiation of agitation, the aqueous solution appeared cloudy or white, and 2,2'-azobis(2-methyl propionamidine)diacrylate in the form of white fine particles with an average particle diameter of 10 gm was generated. Five minutes later from the initiation of agitation, the amount of 2,2'-azobis(2-methyl propionamidine) diacrylate generated became 1.4 percent based on the acrylate monomer. The 2,2'-azobis(2-methyl propionamidine) diacrylate was evenly dispersed in the aqueous monomer solution.

At this time, 2.6 parts aqueous 10 percent sodium persulfate solution and 1 part aqueous 1 percent L-ascorbic acid solution were added while agitating the aqueous monomer solution. After the addition, the aqueous monomer solution continued to be agitated.

About seven minutes after the addition of aqueous sodium persulfate solution, the temperature of the aqueous monomer solution reached about 82° C. Thereafter, the aqueous monomer solution was further agitated for 10 minutes while keeping the temperature thereof between 70° C. and 80° C. to polymerize the acrylate monomer. As a result, a hydrogel having cells was obtained.

The resulting hydrogel having cells was removed, and the same operations as in Example 1 were performed to produce a water-absorbent resin. The average pore diameter of the water-absorbent resin was 70 μm. Moreover, various physical properties of the water-absorbent resin were measured by the above-mentioned methods. The water retention capacity was 27 g/g, the residual monomer content was 120 ppm, the water-soluble component content was 5 percent, the dispersion rate was 37 seconds, the dry touch was 4.1 g, and the absorbent capacity under pressure was 11 g/g. The results are shown in Table 1.

EXAMPLE 4

First, 18 parts acrylic acid, 190 parts aqueous 37 percent sodium acrylate solution, 0.154 parts N,N'-methylenebisacrylamide as a cross-linking agent, and 21 parts deionized water were mixed to prepare an aqueous monomer solution. Namely, the aqueous monomer solution is an aqueous 38 percent acrylate monomer solution with a neutralization rate of 75 mole percent.

By bubbling a nitrogen gas into the aqueous monomer solution while keeping the temperature of the aqueous monomer solution at 25° C., dissolved oxygen was removed. Next, 1.34 parts powdered 2,2'-azobis(2-methyl propionamidine)diacrylate prepared by the above-mentioned production method was added while agitating the aqueous monomer solution. Thereafter, the aqueous solution was agitated at 25° C. under the flow of nitrogen. The 2,2'-azobis(2-methyl propionamidine)diacrylate was evenly dispersed in the aqueous monomer solution.

Next, 1.2 parts aqueous 10 percent sodium persulfate solution and 0.5 parts aqueous 1 percent L-ascorbic acid solution were added while agitating the aqueous monomer solution. After the addition, the aqueous monomer solution continued to be agitated.

About 13 minutes after the addition of aqueous sodium persulfate solution, the temperature of the aqueous monomer solution reached about 92° C. Thereafter, the aqueous monomer solution was further agitated for one hour while keeping the temperature thereof between 60° C. and 80° C. to polymerize the acrylate monomer. As a result, a hydrogel having cells was obtained.

The resulting hydrogel having cells was removed, and the same operations as in Example 1 were performed to produce a water-absorbent resin. The average pore diameter of the water-absorbent resin was 65 μm. Moreover, various physical properties of the water-absorbent resin were measured by the above-mentioned methods. The water retention capacity was 27 g/g, the residual monomer content was 220 ppm, the water-soluble component content was 9 percent, the dispersion rate was 25 seconds, the dry touch was 4.3 g, and the absorbent capacity under pressure was 9 g/g. The results are shown in Table 1.

EXAMPLE 5

First, 21.6 parts acrylic acid, 178 parts aqueous 37 percent sodium acrylate solution, 0.046 parts N,N'-methylenebisacrylamide, 0.18 parts hydroxylethyl cellulose as water-soluble polymer (dispersion stabilizer), and 50 parts deionized water were mixed to prepare an aqueous monomer solution. Namely, the aqueous monomer solution is an aqueous 38 percent acrylate monomer solution with a neutralization rate of 70 mole percent.

By bubbling a nitrogen gas into the aqueous monomer solution while keeping the temperature of the aqueous monomer solution at 25° C., dissolved oxygen was removed. Subsequently, 0.18 parts polyoxyethylene sorbitan monostearate as a surface active agent (dispersion stabilizer), and 2.63 parts ground calcium carbonate as a blowing agent were added while agitating the aqueous monomer solution. The calcium carbonate had an average particle diameter of 3 μm, and was evenly dispersed in the aqueous monomer solution.

Next, 1.2 parts aqueous 10 percent sodium persulfate solution and 0.5 parts aqueous 1 percent L-ascorbic acid solution were added while agitating the aqueous monomer solution at 25° C. under the flow of nitrogen. After sufficiently agitating the aqueous monomer solution, it was left at rest.

About 10 minutes after the addition of aqueous sodium persulfate solution, the temperature of the aqueous monomer solution reached about 99° C. Thereafter, the aqueous monomer solution was further agitated for 10 minutes while keeping the temperature thereof between 60° C. and 80° C. to polymerize the acrylate monomer. As a result, a hydrogel having cells was obtained.

The resulting hydrogel having cells was removed, and the same operations as in Example 1 were performed to produce a water-absorbent resin. The average pore diameter of the water-absorbent resin was 250 μm. Moreover, various physical properties of the water-absorbent resin were measured by the above-mentioned methods. The water retention capacity was 45 g/g, the residual monomer content was 520 ppm, the water-soluble component content was 13 percent, the dispersion rate was 24 seconds, the dry touch was 4.5 g, and the absorbent capacity under pressure was 8 g/g. The results are shown in Table 1.

COMPARATIVE EXAMPLE 1

An aqueous monomer solution was prepared in the same manner as in Example 1. By bubbling a nitrogen gas into the aqueous monomer solution while keeping the temperature of the aqueous monomer solution at 25° C., dissolved oxygen was removed. Next, 4.3 parts aqueous 10 percent 2,2'-azobis (2-methyl propionamidine)dihydrochloride solution was added to the aqueous monomer solution, and dissolved therein. Thereafter, 2.6 parts aqueous 10 percent sodium persulfate solution and 1 part aqueous 1 percent L-ascorbic acid solution were immediately added while agitating the aqueous monomer solution. After the addition, the aqueous monomer solution continued to be agitated, and was left at rest upon the initiation of polymerization. Namely, the acrylate monomer was polymerized without using the blowing agent of the present invention.

About 10 minutes after the addition of aqueous sodium persulfate solution, the temperature of the aqueous monomer solution reached about 95° C. Thereafter, the aqueous monomer solution was further agitated for 10 minutes while keeping the temperature thereof between 70° C. and 85° C. to polymerize the acrylate monomer. As a result, a hydrogel having substantially no cell was obtained. The hydrogel had a few cells ranging from 2 mm to 4 mm in size.

Figure 7:
FIG. 7 is a photograph as a drawing showing the structure of particles of a water-absorbent resin obtained in Comparative Example 1.

The resulting hydrogel was removed, and the same operations as in Example 1 were performed to produce a comparative water-absorbent resin. The comparative water-absorbent resin had no pores. Moreover, various physical properties of the comparative water-absorbent resin were measured by the above-mentioned methods. The water retention capacity was 29 g/g, the residual monomer content was 540 ppm, the water-soluble component content was 14 percent, the dispersion rate was 63 seconds, the dry touch was 6.1 g, and the absorbent capacity under pressure was 7 g/g. Thus, the comparative water-absorbent resin had declined dispersion rate and dry touch. The results are shown in Table 1. FIG. 7 shows an electron photomicrograph indicating the particle structure of the comparative water-absorbent resin having a particle diameter ranging from 300 μm to 600 μm.

COMPARATIVE EXAMPLE 2

First, 21.6 parts acrylic acid, 178 parts aqueous 37 percent sodium acrylate solution, 0.046 parts N,N'-methylenebisacrylamide, and 50 parts deionized water were mixed to prepare an aqueous monomer solution. By bubbling a nitrogen gas into the aqueous monomer solution while keeping the temperature of the aqueous monomer solution at 25° C., dissolved oxygen was removed. Next, 2.63 parts sodium carbonate as a blowing agent was added while agitating the aqueous monomer solution.

As a result, since carbon dioxide gas was generated, 1.2 parts aqueous 10 percent sodium persulfate solution and 0.5 parts aqueous 1 percent L-ascorbic acid solution were immediately added while agitating the aqueous monomer solution. After the addition, the aqueous monomer solution continued to be agitated. In this case, calcium carbonate was not dispersed in the aqueous monomer solution.

About 10 minutes after the addition of aqueous sodium persulfate solution, the temperature of the aqueous monomer solution reached about 97° C. Thereafter, the aqueous monomer solution was further agitated for 10 minutes while keeping the temperature thereof between 60° C. and 80° C. to polymerize the acrylate monomer. As a result, a hydrogel having cells was obtained.

The resulting hydrogel having cells was removed, and the same operations as in Example 1 were performed to produce a comparative water-absorbent resin. The average pore diameter of the comparative water-absorbent resin was about 600 μm. Moreover, various physical properties of the comparative water-absorbent resin were measured by the above-mentioned methods. The water retention capacity was 40 g/g, the residual monomer content was 3,400 ppm, the water-soluble component content was 17 percent, the dispersion rate was 47 seconds, the dry touch was 6.5 g, and the absorbent capacity under pressure was 7 g/g. Thus, the comparative water-absorbent resin have increased residual monomer and water-soluble component contents, and declined dispersion rate and dry touch. The results are shown in Table 1.

EXAMPLE 6

The water-absorbent resin obtained in Example 1 was subjected to secondary cross-linking treatment. First, 0.05 parts ethylene glycol diglycidyl ether and 0.75 parts glycerin as surface cross-linking agents, 0.5 parts lactic acid as a mixing assistant, 3 parts water as a hydrophilic solvent, and 0.75 parts isopropyl alcohol were mixed to prepare a mixed solution.

Next, 100 parts water-absorbent resin produced in Example 1 and the mixed solution were combined, and the resulting mixture was heated at 195° C. for 20 minutes. As a result, a water-absorbent resin having a covalent bond and improved cross-link density in the vicinity of surface, i.e., a water-absorbent resin which underwent the secondary cross-linking treatment, was obtained. The average pore diameter of the water-absorbent resin was 60 μm. Moreover, various physical properties of the water-absorbent resin were measured by the above-mentioned methods. The water retention capacity was 27 g/g, the residual monomer content was 180 ppm, the water-soluble component content was 9 percent, the dispersion rate was 28 seconds, the dry touch was 3.4 g, and the absorbent capacity under pressure was 30 g/g. The results are shown in Table 1.

EXAMPLE 7

The water-absorbent resin obtained in Example 2 was subjected to secondary cross-linking treatment. First, 1 part glycerin, 3 parts water, and 1.75 parts isopropyl alcohol were mixed to prepare a mixed solution.

Next, 100 parts water-absorbent resin produced in Example 2 and the mixed solution were combined, and the resulting mixture was heated at 195° C. for 25 minutes. As a result, a water-absorbent resin having a covalent bond and improved cross-link density in the vicinity of surface, i.e., a water-absorbent resin which underwent the secondary cross-linking treatment, was obtained. The average pore diameter of the water-absorbent resin was 70 μm. Moreover, various physical properties of the water-absorbent resin were measured by the above-mentioned methods. The water retention capacity was 30 g/g, the residual monomer content was 160 ppm, the water-soluble component content was 6 percent, the dispersion rate was 30 seconds, the dry touch was 2.9 g, and the absorbent capacity under pressure was 31 gig. The results are shown in Table 1.

EXAMPLE 8

The water-absorbent resin obtained in Example 3 was subjected to secondary cross-linking treatment. First, 0.05 parts ethylene glycol diglycidyl ether, 0.75 parts glycerin, 0.5 parts polyaspartic acid as a mixing assistant, 3 parts water, and 5 parts isopropyl alcohol were mixed to prepare a mixed solution.

Next, 100 parts water-absorbent resin produced in Example 3 and the mixed solution were combined, and the resulting mixture was heated at 195° C. for 15 minutes. As a result, a water-absorbent resin having a covalent bond and improved cross-link density in the vicinity of surface, i.e., a water-absorbent resin which underwent the secondary cross-linking treatment, was obtained. The average pore diameter of the water-absorbent resin was 70 μm. Moreover, various physical properties of the water-absorbent resin were measured by the above-mentioned methods. The water retention capacity was 26 g/g, the residual monomer content was 120 ppm, the water-soluble component content was 5 percent, the dispersion rate was 35 seconds, the dry touch was 3.3 g, and the absorbent capacity under pressure was 29 g/g. The results are shown in Table 1.

EXAMPLE 9

The water-absorbent resin obtained in Example 6 was further subjected to cross-linking treatment. More specifically, 100 parts water-absorbent resin produced in Example 6 and 5 parts aqueous 30 percent solution of polyethylene imine having an average molecular weight of 70,000 was combined, and the resulting mixture was heated. As a result, a water-absorbent resin having an ionic bond and further improved cross-link density in the vicinity of surface was obtained. The resulting water-absorbent resin had further improved physical properties than the water-absorbent resin before the treatment.

The water-absorbent resins obtained in Examples 7 and 8 also underwent the above-mentioned treatment. The resulting water-absorbent resins had further improved physical properties than the water-absorbent resins before the treatment.

COMPARATIVE EXAMPLE 3

The comparative water-absorbent resin obtained in Comparative Example 2 was subjected to secondary cross-linking treatment. First, 0.05 parts ethylene glycol diglycidyl ether, 0.75 parts glycerin, 0.5 parts lactic acid, 3 parts water, and 0.75 parts isopropyl alcohol were mixed to prepare a mixed solution.

Next, 100 parts comparative water-absorbent resin produced in Comparative Example 2 and the mixed solution were combined, and the resulting mixture was heated at 195 ° C. for 20 minutes. As a result, a comparative water-absorbent resin having a covalent bond and improved cross-link density in the vicinity of surface, i.e., a comparative water-absorbent resin which underwent the secondary cross-linking treatment, was obtained. The average pore diameter of the comparative water-absorbent resin was about 600 μm. Moreover, various physical properties of the comparative water-absorbent resin were measured by the above-mentioned methods. The water retention capacity was 35 g/g, the residual monomer content was 3,400 ppm, the water-soluble component content was 17 percent, the dispersion rate was 40 seconds, the dry touch was 5.5 g, and the absorbent capacity under pressure was 23 g/g. Thus, the resulting comparative resin had increased residual monomer and water-soluble component contents, and declined dispersion rate and dry touch. The results are shown in Table 1.

(azeotropic dehydration). By filtering the cyclohexane solution, a water-absorbent resin in the spherical form with

TABLE 1

|  | Water retention capacity (g/g) | Residual monomer content (ppm) | Water-soluble component content (percent) | Dispersion rate (second) | Dry touch (g) | Water absorbent capacity under pressure (g/g) | Average pore diameter (μm) |
| --- | --- | --- | --- | --- | --- | --- | --- |
| Examples |  |  |  |  |  |  |  |
| 1 | 29 | 200 | 9 | 33 | 4.3 | 11 | 60 |
| 2 | 33 | 170 | 6 | 30 | 3.9 | 12 | 70 |
| 3 | 27 | 120 | 5 | 37 | 4.1 | 11 | 70 |
| 4 | 27 | 220 | 9 | 25 | 4.3 | 9 | 65 |
| 5 | 45 | 520 | 13 | 24 | 4.5 | 8 | 250 |
| 6 | 27 | 180 | 9 | 28 | 3.4 | 30 | 60 |
| 7 | 30 | 160 | 6 | 30 | 2.9 | 31 | 70 |
| 8 | 26 | 120 | 5 | 35 | 3.3 | 29 | 70 |
| Comparative examples |  |  |  |  |  |  |  |
| 1 | 29 | 540 | 14 | 63 | 6.1 | 7 | — |
| 2 | 40 | 3400 | 17 | 47 | 6.5 | 7 | 600 |
| 3 | 35 | 3400 | 17 | 40 | 5.5 | 23 | 600 |

EXAMPLE 10

Dissolved oxygen was removed by bubbling a nitrogen gas into the solution while keeping the temperature of 166 parts aqueous 37 percent sodium acrylate solution at 25° C. Next, 47 parts aqueous 10 percent 2,2'-azobis(2-methyl propionamidine) dihydrochloride solution was added while agitating the aqueous solution. Thereafter, the aqueous solution was agitated at 25° C. under the flow of nitrogen.

About one minute later from the initiation of agitation, the aqueous solution appeared cloudy or white, and 2,2'-azobis (2-methyl propionamidine)diacrylate in the form of white fine particles with an average particle diameter of 15 μm was generated. The 2,2'-azobis(2-methyl propionamidine) diacrylate was evenly dispersed in the aqueous solution.

At this time (one minute later from the initiation of agitation), 425 parts acrylic acid and 5.23 parts trimethylolpropane triacrylate were mixed and dissolved while agitating the aqueous solution to prepare an aqueous monomer solution in which the 2,2'-azobis(2-methyl propionamidine) diacrylate was evenly dispersed (hereinafter just referred to as the aqueous monomer solution). Namely, the aqueous monomer solution is an aqueous 38 percent acrylate monomer solution having a neutralization rate of 75 mole percent.

Meanwhile, a 2L separable flask equipped with an agitator, a reflux condenser, a thermometer, a dropping funnel and a nitrogen gas inlet tube was used as a reaction container 4 grams of sucrose fatty acid ester (trade name: DK-ESTER F-50, produced by Dai-ichi Kogyo Seiyaku Ltd.) as a dispersion stabilizer, and cyclohexane 2 L as a solvent were placed in the reaction container. Moreover, 300 grams of aqueous monomer solution mentioned above was placed in the dropping funnel.

The aqueous monomer solution was dropped while agitating the cyclohexane solution at 230 rpm to disperse and suspend the aqueous monomer solution. Next, the cyclohexane solution was agitated at 60° C. for two hours to perform reversed-phase suspension polymerization of the acrylate monomer. Thereafter, water generated by the reaction was removed by forming an azeotropic with cyclohexane (azeotropic dehydration). By filtering the cyclohexane solution, a water-absorbent resin in the spherical form with an average particle diameter of several hundred μm, i.e., a water-absorbent resin of the present invention, was obtained.

The average pore diameter of the water-absorbent resin was 50 μm. Moreover, various physical properties of the water-absorbent resin were measured by the above-mentioned methods. The water retention capacity was 30 g/g, the residual monomer content was 70 ppm, the water-soluble component content was 9 percent, the dispersion rate was 40 seconds, the dry touch was 4.5 g, and the absorbent capacity under pressure was 10 g/g. The results are shown in Table 2.

EXAMPLE 11

First, 216 parts acrylic acid, 4,321 parts aqueous 37 percent sodium acrylate solution, 5.8 parts polyethylene glycol diacrylate, and 887 parts water were mixed to prepare an aqueous monomer solution. Namely, the aqueous monomer solution is an aqueous 33 percent acrylate monomer solution having a neutralization rate of 85 mole percent.

Dissolved oxygen was removed by bubbling a nitrogen gas into the solution while keeping the temperature of the aqueous monomer solution at 25° C. Next, 40 parts aqueous 10 percent 2,2'-azobis (2-methyl propionamidine) dihydrochloride solution was added while agitating the aqueous monomer solution. Thereafter, the aqueous solution was agitated at 25° C. under the flow of nitrogen.

About six minutes later from the initiation of agitation, the aqueous solution appeared cloudy or white, and 2,2'-azobis (2-methyl propionamidine)diacrylate in the form of white fine particles with an average particle diameter of 7 μm was generated. The 2,2'-azobis(2-methyl propion amidine) diacrylate was evenly dispersed in the aqueous monomer solution.

At this time, 28 parts aqueous 10 percent sodium persulfate solution and 1.3 parts aqueous 1 percent L-ascorbic acid solution were added while agitating the aqueous monomer solution. After the addition, the aqueous monomer solution continued to be agitated.

About 30 seconds after the addition of aqueous sodium persulfate solution, polymerization of the acrylate monomer was initiated. As a result, a hydrogel having cells was obtained.

Figure 5:
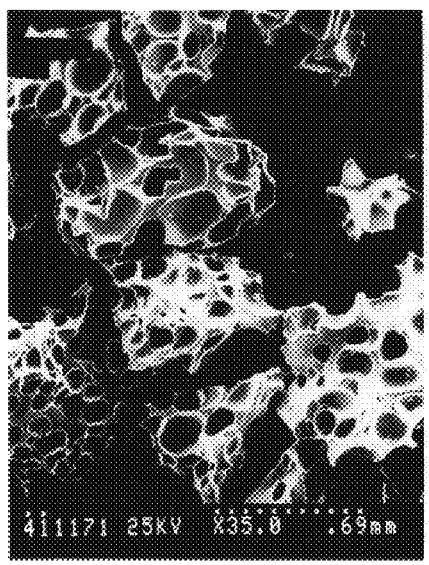
FIG. 5 is a photograph as a drawing, indicating the structure of particles of a water-absorbent resin obtained in Example 11.

The resulting hydrogel having cells was removed, and the same operations as in Example 1 were performed to produce a water-absorbent resin. The average pore diameter of the water-absorbent resin was 50 μm. Moreover, various physical properties of the water-absorbent resin were measured by the above-mentioned methods. The water retention capacity was 39 g/g, the residual monomer content was 240 ppm, the water-soluble component content was 8 percent, the dispersion rate was 21 seconds, the dry touch was 4.0 g, and the absorbent capacity under pressure was 11 g/g. The results are shown in Table 2. FIG. 5 shows an electron photomicrograph indicating the particle structure of a water-absorbent resin having a particle diameter ranging from 300 μm to 600 μm.

EXAMPLE 12

First, 375 parts acrylic acid, 5,290 parts aqueous 37 percent sodium acrylate solution, 6.3 parts polyethylene glycol diacrylate, and 808 parts water were mixed to prepare an aqueous monomer solution. Namely, the aqueous monomer solution is an aqueous 35.5 percent acrylate monomer solution having a neutralization rate of 85 mole percent.

Dissolved oxygen was removed by bubbling a nitrogen gas into the solution while keeping the temperature of the aqueous monomer solution at 25° C. Next, 52 parts aqueous 10 percent 2,2'-azobis (2-methyl propionamidine) dihydrochloride solution was added while agitating the aqueous monomer solution. Thereafter, the aqueous solution was agitated at 25° C. under the flow of nitrogen.

About 2.5 minutes later from the initiation of agitation, the aqueous solution appeared cloudy or white, and 2,2'-azobis(2-methyl propionamidine)diacrylate in the form of white fine particles with an average particle diameter of 9 μm was generated. The 2,2'-azobis(2-methyl propionamidine)diacrylate was evenly dispersed in the aqueous monomer solution.

At this point, 36 parts aqueous 10 percent sodium persulfate solution-and 1.7 parts aqueous 1 percent L-ascorbic acid solution were added while agitating the aqueous monomer solution. After the addition, the aqueous monomer solution continued to be agitated.

About 30 seconds after the addition of aqueous sodium persulfate solution, polymerization of the acrylate monomer was initiated. As a result, a hydrogel having cells was obtained.

The resulting hydrogel having cells was removed, and the same operations as in Example 1 were performed to produce a water-absorbent resin. The average pore diameter of the water-absorbent resin was 100 μm. Moreover, various physical properties of the water-absorbent resin were measured by the above-mentioned methods. The water retention capacity was 38 g/g, the residual monomer content was 270 ppm, the water-soluble component content was 9 percent, the dispersion rate was 24 seconds, the dry touch was 4.0 g, and the absorbent capacity under pressure was 10 g/g. The results are shown in Table 2.

EXAMPLE 13

First, 375 parts acrylic acid, 5,290 parts aqueous 37 percent sodium acrylate solution, and 6.3 parts polyethylene glycol diacrylate were mixed to prepare an aqueous monomer solution. Namely, the aqueous monomer solution is an aqueous about 42 percent acrylate monomer solution having a neutralization rate of 85 mole percent.

Dissolved oxygen was removed by bubbling a nitrogen gas into the solution while keeping the temperature of the aqueous monomer solution at 25° C. Next, 52 parts aqueous 10 percent 2,2-azobis (2-methyl propionamidine) dihydrochloride solution was added while agitating the aqueous monomer solution. Thereafter, the aqueous solution was agitated at 25° C. under the flow of nitrogen.

About 2.5 minutes later from the initiation of agitation, the aqueous solution appeared cloudy or white, and 2,2'-azobis(2-methyl propionamidine)diacrylate in the form of white fine particles with an average particle diameter of 9 μm was generated. The 2,2'-azobis(2-methyl propionamidine)diacrylate was evenly dispersed in the aqueous monomer solution.

At this point, the concentration of the acrylate monomer was diluted from about 42 percent to about 35.5 percent by adding 808 parts water to the aqueous monomer solution. Thereafter, 306 parts aqueous 10 percent sodium persulfate solution and 1.7 parts aqueous 1 percent L-ascorbic acid solution were added while agitating the aqueous monomer solution to prepare an aqueous monomer solution. After the addition, the aqueous monomer solution continued to be agitated.

About 30 seconds after the addition of aqueous sodium persulfate solution, polymerization of the acrylate monomer was initiated. As a result, a hydrogel having cells was obtained.

The resulting hydrogel having cells was removed, and the same operations as in Example 1 were performed to produce a water-absorbent resin. The average pore diameter of the water-absorbent resin was 100 μm. Moreover, various physical properties of the water-absorbent resin were measured by the above-mentioned methods. The water retention capacity was 38 g/g, the residual monomer content was 270 ppm, the water-soluble component content was 9 percent, the dispersion rate was 23 seconds, the dry touch was 4.1 g, and the absorbent capacity under pressure was 10 g/g. The results are shown in Table 2.

EXAMPLE 14

First, by performing the same polymerization as in Example 1, a hydrogel having cells was obtained. More specifically, by leaving the aqueous monomer solution statically to polymerize the acrylate monomer, the hydrogel having cells as a porous cross-linked polymer was produced.

The resulting hydrogel having cells was removed and cut into a sheet with a thickness of about 5 mm. Thereafter, a microwave was radiated to the hydrogel having cells using a home-use microwave with a frequency of 2,450 MHz (trade name: NE-A460, produced by Matsushita Electric Industrial Co., Ltd.). About 30 seconds after the initiation of radiation, the hydrogel having cells was dried in a state in which it was swelled to a size about 10 times larger than the size before radiated. Thus, a sheet of water-absorbent resin of the present invention was produced.

Figure 6:
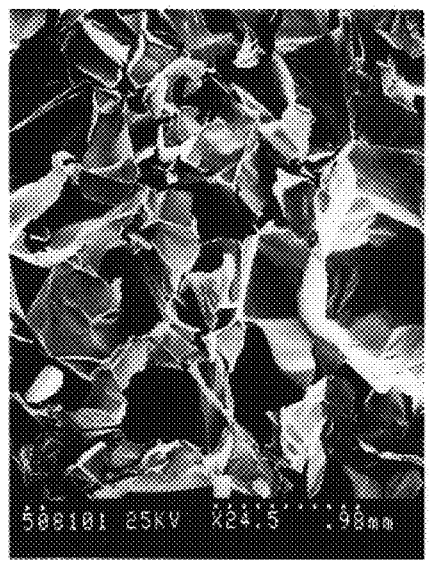
FIG. 6 is an electron photomicrograph as a drawing, indicating the structure of the profile of a water-absorbent resin obtained in Example 14.

The average pore diameter of the water-absorbent resin was about 500 μm. Moreover, various physical properties of the water-absorbent resin were measured by the above-mentioned methods. The water retention capacity was 31 g/g, the residual monomer content was 170 ppm, the water-soluble component content was 10 percent, the dispersion rate was 19 seconds, the dry touch was 4.3 g, and the absorbent capacity under pressure was 9 g/g. The results are shown in Table 2. FIG. 6 shows an electron photomicrograph indicating the profile structure of the sheet of water-absorbent resin.

EXAMPLE 15

First, by performing the same polymerization as in Example 1, a hydrogel having cells was obtained. More specifically, by leaving the aqueous monomer solution at rest to polymerize the acrylate monomer, the hydrogel having cells as a porous cross-linked polymer was produced.

The resulting hydrogel having cells was removed and cut into a sheet with a thickness of about 5 mm. Thereafter, the hydrogel having cells was hot-air dried at 170° C. using a hot-air drier. The hydrogel having cells was dried in a state in which it was swelled into a size about 1.5 times larger than the original size. Thus, a sheet of water-absorbent resin of the present invention was produced.

The average pore diameter of the water-absorbent resin was 250 μm. Moreover, various physical properties of the water-absorbent resin were measured by the above-mentioned methods. The water retention capacity was 30 g/g, the residual monomer content was 200 ppm, the water-soluble component content was 9 percent, the dispersion rate was 24 seconds, the dry touch was 4.5 g, and the absorbent capacity under pressure was 9 g/g. The results are shown in Table 2.

EXAMPLE 16

The water-absorbent resin obtained in Example 13 was subjected to secondary cross-linking treatment. First, 0.05 parts ethylene glycol diglycidyl ether, 0.75 parts glycerin, 0.5 parts lactic acid, 3 parts water, and 0.75 parts isopropyl alcohol were mixed to prepare a mixed solution.

Next, 100 parts water-absorbent resin produced in Example 13 and the mixed solution were combined, and the resulting mixture was heated at 195° C. for 20 minutes. As a result, a water-absorbent resin having a covalent bond and improved cross-link density in the vicinity of surface, i.e., a water-absorbent resin which underwent the secondary cross-linking treatment, was obtained. The average pore diameter of the water-absorbent resin was 600 μm. Moreover, various physical properties of the water-absorbent resin were measured by the above-mentioned methods. The water retention capacity was 35 g/g, the residual monomer content was 250 ppm, the water-soluble component content was 9 percent, the dispersion rate was 14 seconds, the dry touch was 3.5 g, and the absorbent capacity under pressure was 33 g/g. The results are shown in Table 2.

COMPARATIVE EXAMPLE 4

First, by performing the same polymerization as in Comparative Example 1, a hydrogel was produced. More specifically, by leaving the aqueous monomer solution at rest to polymerize the acrylate monomer, the hydrogel was produced.

The resulting hydrogel was removed and cut into a sheet with a thickness of about 5 mm. Thereafter, a microwave was radiated to the hydrogel using a home-use microwave so as to dry the hydrogel. As a result, a sheet of water-absorbent resin was obtained for comparison purposes. However, a discharge phenomenon occurred at a part of the surface of the hydrogel during drying, and the part was burnt black.

This comparative water-absorbent resin had no pore. Moreover, various physical properties of the comparative water-absorbent resin were measured by the above-mentioned methods. The water retention capacity was 27 g/g, the residual monomer content was 640 ppm, the water-soluble component- content was 15 percent, the dispersion rate was 83 seconds, the dry touch was 7.1 g, and the absorbent capacity under pressure was 6 g/g. Thus, the comparative water-absorbent resin had declined dispersion rate and dry touch. The results are shown in Table 2.

COMPARATIVE EXAMPLE 5

An aqueous monomer solution was prepared in the same manner as in Example 11. By bubbling a nitrogen gas into the aqueous monomer solution while keeping the temperature of the aqueous monomer solution at 25° C., dissolved oxygen was removed. Next, 40 parts aqueous 10 percent 2,2'-azobis (2-methyl propionamidine) dihydrochloride solution was added while agitating the aqueous monomer solution. 28 parts aqueous 10 percent sodium persulfate solution and 1.3 parts aqueous 1 percent L-ascorbic acid solution were immediately added to the aqueous monomer solution. Thereafter, the acrylate monomer was polymerized by agitating the aqueous monomer solution. As a result, a hydrogel having cells was produced. Namely, the acrylate monomer was polymerized without using a blowing agent of the present invention. The hydrogel had cells ranging from 1 mm to 3 mm in size.

The resulting hydrogel having cells was removed, and the same operations as in Example 1 were performed to produce a comparative water-absorbent resin. The resulting comparative water-absorbent resin had a particle diameter ranging from 850 μm to 10 μm, and almost no pores. Moreover, various physical properties of the comparative water-absorbent resin were measured by the above-mentioned methods. The water retention capacity was 39 g/g, the residual monomer content was 940 ppm, the water-soluble component content was 12 percent, the dispersion rate was 42 seconds, the dry touch was 6.0 g, and the absorbent capacity under pressure was 8 g/g. Thus, the comparative water-absorbent resin had increased residual monomer content, and declined dispersion rate and dry touch. The results are shown in Table 2.

COMPARATIVE EXAMPLE 6

An aqueous monomer solution was prepared in the same manner as in Example 1. By bubbling a nitrogen gas into the aqueous monomer solution while keeping the temperature of the aqueous monomer solution at 25° C., dissolved oxygen was removed. Next, sorbitan monostearate as a surface active agent was added in an amount of 0.2 percent based on the amount of the aqueous monomer solution, and then cyclohexane as a liquid blowing agent was added in an amount of 23 percent based on the amount of the aqueous monomer solution while agitating the aqueous monomer solution. As a result, cyclohexane having an average particle diameter of about 50 μm was evenly dispersed in the aqueous monomer solution.

Thereafter, 2.6 parts aqueous 10 percent sodium persulfate solution and 1 part aqueous 1 percent L-ascorbic acid solution were added while agitating the aqueous monomer solution. After sufficient agitation, the aqueous monomer solution was kept at rest to polymerize the acrylate monomer. As a result, a hydrogel was produced. Namely, the acrylate monomer was polymerized without using a blowing agent of the present invention. The hydrogel had cells ranging from 2 mm to 3 mm in size.

The resulting hydrogel was removed, and the same operations as in Example 1 were performed to produce a comparative water-absorbent resin. The resulting comparative water-absorbent resin had particle diameters ranging from 850 μm to 10 μm, and almost no pores. Moreover, the comparative water-absorbent resin had an odor of cyclohexane.

Various physical properties of the comparative water-absorbent resin were measured by the above-mentioned methods. The water retention capacity was 27 g/g, the residual monomer content was 540 ppm, the water-soluble component content was 12 percent, the dispersion rate was 63 seconds, the dry touch was 7.4 g, and the absorbent capacity under pressure was 7 g/g. Thus, the comparative water-absorbent resin had declined dispersion rate and dry touch. The results are shown in Table 2.

COMPARATIVE EXAMPLE 7

An aqueous monomer solution was prepared in the same manner as in Example 1. By bubbling a nitrogen gas into the aqueous monomer solution while keeping the temperature of the aqueous monomer solution at 25° C., dissolved oxygen was removed. Next, ethylene carbonate as a liquid blowing agent was dissolved in the aqueous monomer solution while agitating the aqueous monomer solution so as to be 1 percent based on the amount of aqueous monomer solution.

Thereafter, 2.6 parts aqueous 10 percent sodium persulfate solution and 1 part aqueous 1 percent L-ascorbic acid solution were added while agitating the aqueous monomer solution. After sufficient agitation, the aqueous monomer solution was kept at rest to polymerize the acrylate monomer. As a result, a hydrogel was produced. Namely, the acrylate monomer was polymerized without using a blowing agent of the present invention. The hydrogel had cells. ranging from 2 mm to 3 mm in size.

The resulting hydrogel was removed, and the same operations as in Example 1 were performed to produce a comparative water-absorbent resin. The resulting comparative water-absorbent resin had particle diameters ranging from 850 $\mu$m to 10 $\mu$m, and almost no pores.

Various physical properties of the comparative water-absorbent resin were measured by the above-mentioned methods. The water retention capacity was 23 g/g, the residual monomer content was 740 ppm, the water-soluble component content was 7 percent, the dispersion rate was 73 seconds, the dry touch was 8.4 g, and the absorbent capacity under pressure was 9 g/g. Thus, the comparative water-absorbent resin had declined dispersion rate and dry touch. The results are shown in Table 2.

specifically, by leaving the aqueous monomer solution at rest to polymerize the acrylate monomer, the hydrogel having cells as a porous cross-linked polymer was produced.

The resulting hydrogel having cells was removed, cut into pieces in size ranging from about 20 mm to 1 mm, and then hot-air-dried at 150° C. with a hot-air drier. Thereafter, the dried pieces were ground with a roll mill, and sieved using a 20-mesh screen, thereby obtaining a water-absorbent resin of the present invention.

It was confirmed through an electron photomicrograph that the resulting water-absorbent resin was porous. The average pore diameter of the water-absorbent resin was 60 $\mu$m. Next, 0.3 parts inorganic powder (trade name: AEROSIL 200, produced by Nippon Aerosil Co., Ltd.) was added to 100 parts water-absorbent resin, and sufficiently mixed, thereby producing a water-absorbent resin composition of the present invention. Various physical properties of the resulting water-absorbent resin composition were measured by the above-mentioned methods. The water retention capacity was 33 g/g, the absorption rate was 77 seconds, and the liquid permeability was 112 seconds. The results are shown in Table 3.

EXAMPLE 18

First, by performing the same polymerization as in Example 2, a hydrogel having cells was obtained. More specifically, by leaving the aqueous monomer solution at rest to polymerize the acrylate monomer, the hydrogel having cells as a porous cross-linked polymer was produced.

The resulting hydrogel having cells was removed, cut into pieces in size ranging from about 20 mm to 1 mm, and then hot-air-dried at 150° C. with a hot-air drier. Thereafter, the dried pieces were ground with a roll mill, and sieved using a 20-mesh screen, thereby obtaining a water-absorbent resin of the present invention.

Next, the water-absorbent resin was subjected to secondary cross-linking treatment. First, 1 part glycerin, 3 parts water and 1 part isopropyl alcohol were mixed to prepare a mixed solution. Subsequently, 100 parts water-absorbent

TABLE 2

|  | Water retention capacity (g/g) | Residual monomer content (ppm) | Water-soluble component content (%) | Dispersion rate (second) | Dry touch (g) | Water absorbent capacity under pressure (g/g) | Average pore diameter ($\mu$m) |
|---|---|---|---|---|---|---|---|
| Examples |  |  |  |  |  |  |  |
| 10 | 30 | 70 | 9 | 40 | 4.5 | 10 | 50 |
| 11 | 39 | 240 | 8 | 21 | 4.0 | 11 | 150 |
| 12 | 38 | 270 | 9 | 24 | 4.0 | 10 | 100 |
| 13 | 38 | 270 | 9 | 23 | 4.1 | 10 | 100 |
| 14 | 31 | 170 | 10 | 19 | 4.3 | 9 | 500 |
| 15 | 30 | 200 | 9 | 24 | 4.5 | 9 | 250 |
| 16 | 35 | 250 | 9 | 14 | 3.5 | 33 | 600 |
| Comparative examples |  |  |  |  |  |  |  |
| 4 | 27 | 640 | 15 | 83 | 7.1 | 6 | — |
| 5 | 39 | 940 | 12 | 42 | 6.0 | 8 | — |
| 6 | 27 | 540 | 12 | 63 | 7.4 | 7 | — |
| 7 | 23 | 740 | 7 | 73 | 8.4 | 9 | — |

EXAMPLE 17

First, by performing the same polymerization as in Example 1, a hydrogel having cells was obtained. More resin and the mixed solution were combined, and the resulting mixture was heated at 195° C. for 25 minutes. As a result, a water-absorbent resin having a covalent bond and improved cross-link density in the vicinity of surface, i.e., a water-absorbent resin which underwent the secondary cross-linking treatment, was obtained. The average pore diameter of the water-absorbent resin was 70 μm. The residual monomer content was 150 ppm, the water-soluble component content was 5 percent, and the absorbent capacity under pressure was 31 g/g.

Next, 0.3 parts inorganic powder (trade name: AEROSIL 200, produced by Nippon Aerosl Co., Ltd.) was added to 100 parts water-absorbent resin, and sufficiently mixed, thereby producing a water-absorbent resin composition of the present invention. Various physical properties of the resulting water-absorbent resin composition were measured by the above-mentioned methods. The water retention capacity was 31 g/g, the absorption rate. was 66 seconds, and the liquid permeability under pressure was 32 seconds. The results are shown in Table 3.

EXAMPLE 19

First, 38.6 parts acrylic acid, 409 parts aqueous 37 percent sodium acrylate solution, 0.45 parts trimethyloipropane triacrylate, and 53 parts deionized water were mixed to prepare an aqueous monomer solution.

By bubbling a nitrogen gas into the aqueous monomer solution while keeping the temperature of the aqueous monomer solution at 25° C., dissolved oxygen was removed. Next, 4.3 parts aqueous 10 percent 2,2'-azobis(2-methyl propionamidine)dihydrochloride solution was added while agitating the aqueous monomer solution. Thereafter, the aqueous solution was agitated at 25° C. under the flow of nitrogen.

About seven minutes later from the initiation of agitation, the aqueous solution appeared cloudy or white, and 2,2'-azobis(2-methyl propionamidine)diacrylate in the form of white fine solid particles with an average particle diameter of 9 um was generated. Moreover, 11 minutes later from the initiation of agitation, the amount of 2,2'-azobis (2-methyl propionamidine) diacrylate generated became 0.32 percent based on the acrylate monomer. The 2,2'-azobis (2-methyl propionamidine) diacrylate was evenly dispersed in the aqueous monomer solution.

At this time, 2.6 parts aqueous 10 percent sodium persulfate solution and 1 part aqueous 1 percent L-ascorbic acid solution were added while agitating the aqueous monomer solution. After the addition, the aqueous monomer solution continued to be agitated.

About 10 minutes after the addition of aqueous sodium persulfate solution, the temperature of the aqueous monomer solution reached about 88° C. Thereafter, the aqueous monomer solution continued to be agitated for further 12 minutes while keeping the temperature thereof between 70° C. and 80° C. so as to polymerize the acrylate monomer. As a result, a hydrogel having cells was obtained.

The resulting hydrogel having cells was removed, made into small pieces in size ranging from about 20 mm to 1 mm, and hot-air-dried at 150° C. with a hot-air drier. Subsequently, the dried pieces were ground with a roll mill, and classified using a 20-mesh screen, thereby producing a water-absorbent resin of the present invention.

Next, the water-absorbent resin was subjected to secondary cross-linking treatment. First, 0.05 parts ethylene glycol diglycidyl ether, 0.75 parts glycerin, 0.5 parts lactic acid, 3 parts water and 0.75 parts isopropyl alcohol were mixed to prepare a mixed solution. Subsequently, 100 parts water-absorbent resin and the mixed solution were combined, and the resulting mixture was heated at 195° C. for 20 minutes.

Furthermore, 5 parts aqueous 30 percent polyethylene imine solution having an average molecular weight of 70,000 was mixed into the mixed solution, and the resulting mixed solution was heated. As a result, a water-absorbent resin having a covalent bond and ionic bond, and improved cross-link density in the vicinity of surface, i.e., a water-absorbent resin which underwent the secondary cross-linking treatment, was obtained.

Thereafter, 0.3 parts inorganic powder (trade name: AEROSIL 200, produced by Nippon Aerosil Co., Ltd.) was added to 100 parts water-absorbent resin, and sufficiently mixed, thereby producing a water-absorbent resin composition of the present invention. Various physical properties of the resulting water-absorbent resin composition were measured by the above-mentioned methods. The water retention capacity was 28 g/g, the absorption rate was 56 seconds, and the liquid permeability was 23 seconds. The results are shown in Table 3.

COMPARATIVE EXAMPLE 8

First, 800 parts acrylic acid, 4 parts tetraallyloxy ethane, and 3,166 parts water were placed in a reaction container to prepare an aqueous monomer solution. By injecting a nitrogen gas into the aqueous monomer solution, dissolved oxygen was removed, and the temperature of the aqueous monomer solution was set at 10° C.

When the dissolved oxygen in the aqueous monomer solution became 1 ppm or less, an aqueous solution formed by dissolving 2.4 parts 2,2'-azobisamidinopropane dihydrochloride in 10 parts water, an aqueous solution produced by dissolving 0.2 parts ascorbic acid in 10 parts water, and an aqueous solution made by diluting 2.29 parts aqueous 35 percent hydrogen peroxide solution with 10 parts water were added in this order as catalysts.

Polymerization was initiated after while from the addition, and the temperature of the aqueous monomer solution became the maximum temperatures ranging from about 65° C. to 70° about two hours later, thereby obtaining a hydrogel. Thereafter, the hydrogel was placed and kept in an insulated container for three hours to reduce the residual monomer content to 1,000 ppm or less.

Then, the hydrogel was removed and cut into small pieces with a mincer. The temperature of the minced hydrogel was about 66° C. Next, 640 parts aqueous 50 percent sodium hydroxide solution was added to the hydrogel. The temperature of the aqueous 50 percent sodium hydroxide solution was 38° C. The aqueous solution was agitated while cutting the hydrogel into smaller pieces in the aqueous solution so as to uniformly perform neutralization. The aqueous solution was heated by the neutralization, and its temperature was raised to temperatures ranging from 88° C. to 93° C.

Next, an aqueous solution formed by dissolving 2.4 parts ethylene glycol diglycidyl ether as a cross-linking agent in 50 parts water was added to the above aqueous solution. The temperature of the ethylene glycol diglycidyl ether was 24° C. The aqueous solution was agitated while cutting the hydrogel into smaller pieces in the aqueous solution so that the ethylene glycol diglycidyl ether was evenly dispersed to achieve a uniform surface cross-linkage.

Then, the hydrogel to which neutralization and surface cross-linking steps were applied was removed, and dried at 105° C. using a rotary drum dryer to arrange the water content in the hydrogel to be 10 percent. As a result, dried pieces in the form of flakes were obtained. Subsequently, the dried pieces were ground and sieved using a 20-mesh screen and a 325-mesh screen, thereby producing a comparative water-absorbent resin composition.

Various physical properties of the resulting comparative water-absorbent resin composition were measured by the above-mentioned methods. The water retention capacity was 31 g/g, the absorption rate was 87 seconds, and the liquid permeability under pressure was 600 seconds. Thus, the comparative water-absorbent resin composition had declined absorption rate and liquid permeability. The results are shown in Table 3.

COMPARATIVE EXAMPLE 9

First, 98.9 grams of aqueous 30 percent sodium hydroxide solution was added to an aqueous solution formed by diluting 72.1 grams acrylic acid with 18.0 grams of water while cooling the aqueous solution for neutralization. Thereafter, 10.7 grams of aqueous 2.8 percent potassium persulfate solution was added to the aqueous solution, thereby forming a uniform solution. As a result, an aqueous monomer solution to which a radical polymerization initiator was added was prepared.

Meanwhile, a 500 ml flask equipped with an agitator, a reflux condenser, a thermometer, a dropping funnel and a nitrogen gas inlet tube was used as a-reaction container. 283 ml of cyclohexane and 2.2 grams of aqueous 25 percent polyoxyethylene dodecyl ether sodium sulfate salt solution were placed in the reaction container, and agitated at 300 rpm, thereby dispersing the polyoxyethylene dodecyl ether sodium sulfate salt. After performing nitrogen substitution in the flask, the temperature was raised to 75° C. Moreover, the aqueous monomer solution was placed in the dropping funnel.

The aqueous monomer solution was dropped in 30 minutes while agitating the cyclohexane solution so as to disperse and suspense the aqueous monomer solution. After dropping the aqueous monomer solution, the cyclohexane solution was agitated at 75° C. for 1.5 hours, and further agitated at 80° C. for four hours so as to perform reverse-phase suspension-polymerization of the acrylate monomer. During polymerization, water in the reaction container was continuously removed by forming an azeotrope with cyclohexane (azeotropic dehydration).

When the amount of water in the reaction container became 30 percent of the amount of water added before the polymerization, 0.18 grams of ethylene glycol diglycidyl ether was added to the reaction container, and reacted for 30 minutes.

After the reaction, the cyclohexane solution was filtered, and the resulting hydrogel was subjected to vacuum drying, thereby obtaining 88.0 grams of (sodium) acrylate polymer. Next, the polymer was ground, and sieved with a 20-mesh screen, thereby producing a comparative water-absorbent resin composition.

Various physical properties of the resulting comparative water-absorbent resin composition were measured by the above-mentioned methods. The water retention capacity was 30 g/g, the absorption rate was 81 seconds, and the liquid permeability was 670 seconds. Thus, the comparative water-absorbent resin composition had declined absorption rate and liquid permeability under pressure. The results are shown in Table 3.

COMPARATIVE EXAMPLE 10

By decomposing commercially available paper diapers, water-absorbent resins were removed. The paper diapers used here were Moony Power-Slim (trade name) produced by Uni Charm Corporation (hereinafter referred to as the product A), Doremi (trade name) produced by Shin Oji Paper Manufacturing Co., Ltd. (hereinafter referred to as the product B), Merries Pants (trade name) produced by Kao Corporation. (hereinafter referred to as the product C), and Moony Man (trade name) produced by Uni Charm Corporation (hereinafter referred to as the product D) Various physical properties of these comparative water-absorbent resins, i.e., the commercially available products A to D, were measured by the above-mentioned methods.

In addition, various physical properties of Sanwet IM-5000 (trade name) produced by Sanyo Chemical Industries, Ltd. (hereinafter referred to as the product E), and Arasorb 720 (trade name) produced by Arakawa Chemical industries, Ltd. (hereinafter referred to as the product F) were measured by the above-mentioned methods.

The results are given in Table 3. The products A to F are inferior at least in the absorption rate or in the liquid permeability under pressure.

TABLE 3

| | Water retention ability (g/g) | Absorption rate (second) | Liquid permeability under pressure (second) |
|---|---|---|---|
| Examples | | | |
| 17 | 33 | 77 | 112 |
| 18 | 31 | 66 | 32 |
| 19 | 28 | 56 | 23 |
| Comparative examples | | | |
| 8 | 30 | 81 | 670 |
| 9 | 31 | 87 | not less than 600 |
| Comparative example 10 | | | |
| product A | 31 | 43 | 254 |
| product B | 26 | 33 | not less than 1000 |
| product C | 29 | 37 | not less than 600 |
| product D | 38 | 87 | not less than 1000 |
| product E | 30 | 48 | not less than 600 |
| product F | 20 | 8 | 512 |

While particular embodiments or examples of the present invention have been described to carry out the invention in the best mode, it will be obvious that the same may be varied in many ways Such variations are not to be regarded as a departure from the spirit and scope of the invention, and all such modifications as would be obvious to one skilled in the art are intended to be included within the scope of the following claims.

APPLICATIONS OF THE INVENTION TO INDUSTRIAL USE

With the use of the above-mentioned methods, it is possible to industrially produce water-absorbent resins having excellent water absorption characteristics, such as dispersion and absorption rate of aqueous fluid, water retention capacity and dry touch, lower water-soluble component content, and lower residual monomer content, in an inexpensive and easy manner.

Moreover, the above-mentioned structures can provide water-absorbent resins and water-absorbent resin compositions which achieve excellent permeability and dispersion of aqueous fluid under pressure, and improved absorption rate and water retention capacity without causing a gel blocking phenomenon.

The water-absorbent resins and the water-absorbent resin compositions can be suitably used in absorbent articles in various fields, for example: sanitary materials (body fluids absorbent articles) such as paper diapers, sanitary napkins, incontinence pads, wound protecting material and wound healing material; absorbent articles for absorbing urine of pets; materials of construction and building; such as building material, water retentive material for soil, waterproof material, packing material, and gel pusule; materials for food, such as drip absorbing material, freshness retentive material, and heat insulating material; various industrial articles, such as oil and water separating material, condensation preventing material, and coagulant; and agricultural and horticultural articles, such as water retentive material for plant and soil. Thus, it is possible to provide absorbent articles exhibiting excellent performances mentioned above.

What is claimed is:

1. A process for producing a water-absorbent resin comprising the steps of:
    polymerizing an unsaturated monomer after dispersing a solid blowing agent having an average particle diameter within a range of from 1 μm to 100 μm in an aqueous monomer solution containing said unsaturated monomer and a cross-linking agent; and
    forming a covalent, bond by treating a vicinity of a surface of said water-adsorbent resin with a surface cross-linking agent after said polymerizing step;
    wherein at least one condition selected from the group consisting of conditions (a), (b) and (c) is satisfied:
    (a) said blowing agent is an acrylic acid salt of an azo compound containing an amino group represented by formula (1)

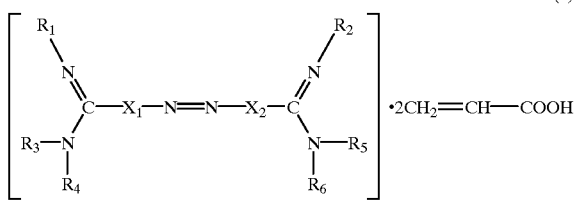

(b) said blowing agent is an acrylic acid salt of an azo compound containing an amino group represented by formula (2)

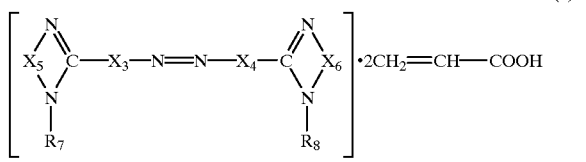

(c) the step of polymerizing said unsaturated monomer i, carried out under the presence of a dispersion stabilizer.

2. The process for producing a water-absorbent resin according to claim 1,
    wherein the step of polymerizing said unsaturated monomer is carried out while agitating said aqueous monomer solution.

3. The process for producing a water-absorbent resin according to claim 1,
    wherein the step of polymerizing said unsaturated monomer is carried out without agitating said aqueous monomer solution.

4. The process for producing a water-absorbent resin according to claim 1,
    wherein the step of polymerizing said unsaturated monomer is carried out .at temperature s ranging from 40° C. to 120° C.

5. The process for producing a water-absorbent resin according to claim 1,
    wherein said unsaturated monomer contains at least one kind of acrylate monomer selected from the group consisting of acrylic acids and water-soluble salts of the acrylic acids as a chief constituent.

6. The process for producing a water-absorbent resin according to claim 5,
    wherein said water-soluble salt is-at least one kind of salt selected from the group consisting of sodium salt and potassium salt.

7. The process for producing a water-absorbent resin according to claim 1,
    wherein said cross-linking agent is at least one kind of agent selected from the group consisting of compounds having a plurality of vinyl groups in a molecule, compounds having in a molecule at least one vinyl group and at least one functional group reactive with a carboxyl group of said unsaturated monomer, and compounds having in a molecule a plurality of functional groups reactive with said carboxyl group.

8. The process for producing a water-absorbent resin according to claim 1,
    wherein said blowing agent is used in an amount ranging from 0.005 weight parts to 25 weight parts based on 100 weight parts of said unsaturated monomer.

9. The process for producing a water-absorbent resin according to claim 1,
    wherein said blowing agent is an acrylic acid salt of an azo compound containing an amino group represented by general formula (1)

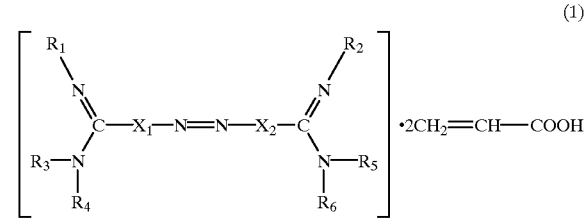

(wherein $X_1$ and $X_2$ independently represent an alkylene group having 1 to 4 carbons, $R_1$, $R_2$, $R_3$, $R_4$, $R_5$, and $R_6$ independently represent a hydrogen atom, alkyl group having 1 to 4 carbons, aryl group, allyl group or benzyl group).

10. The process for producing a water-absorbent resin according to claim 1,
    wherein said blowing agent is an acrylic acid salt of an azo compound containing an amino group represented by general formula (2)

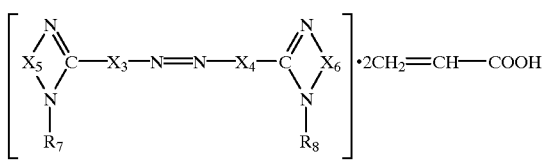 (2)

(wherein $X_3$ and $X_4$ independently represent an alkylene group having 1 to 4 carbons, $X_5$ and $X_6$ independently represent an alkylene group having 2 to 4 carbons, and $R_7$ and $R_8$ independently represent a hydrogen atom or alkyl group having 1 to 4 carbons).

11. The process for producing a water-absorbent resin according to claim 1,
wherein said blowing agent is 2,2'-azobis(2-methyl propion amidine) diacrylate.

12. The process for producing a water-absorbent resin according to claim 1, further comprising the step of precipitating said blowing agent in said aqueous monomer solution after dissolving a blowing agent precursor in said aqueous monomer solution prior to the step of polymerizing said unsaturated monomer.

13. The process for producing a water-absorbent resin according to claim 12,
wherein the step of precipitating said blowing agent includes reacting said blowing agent precursor with said unsaturated monomer.

14. The process for producing a water-absorbent resin according to claim 12,
wherein said blowing agent precursor is a hydrochloride of an azo compound containing an amino group.

15. The process for producing a water-absorbent resin according to claim 1,
wherein the step of polymerizing said unsaturated monomer is carried out under the presence of a dispersion stabilizer.

16. The process, for producing a water-absorbent resin according to claim 15,
wherein said dispersion stabilizer is a surface active agent.

17. The process for producing a water-absorbent resin according to claim 15,
wherein said dispersion stabilizer is a water-soluble polymer.

18. The process for producing a water-absorbent resin according to claim 15,
wherein said dispersion stabilizer is at least one kind of agent selected from the group consisting of polyvinyl alcohol, starch and derivatives thereof, and cellulose and derivatives thereof.

19. The process for producing a water-absorbent resin according to claim 1, further comprising the step of forming a covalent bond by treating a vicinity of a surface of said water-absorbent resin with a surface cross-linking agent after the step of polymerizing said unsaturated monomer.

20. The process for producing a water-absorbent resin according to claim 19,
wherein said surface cross-linking agent is a compound having a plurality of functional groups capable of forming a covalent bond by reacting with a carboxyl group of said water-absorbent resin.

21. The process for producing a water-absorbent resin according to claim 19,
wherein said surface cross-linking agent is at least one kind of agent selected from the group consisting of polyhydric alcohol compounds, epoxy compounds, polyamine compounds, condensation products of polyamine compound and haloepoxy compound, and alkylene carbonate compounds.

22. The process for producing a water-absorbent resin according to claim 19, further comprising the step of forming an ionic bond by treating the vicinity of the surface of said water-absorbent resin with a cationic compound after the step of forming the covalent bond.

23. The process for producing a water-absorbent resin according to claim 22,
wherein said cationic compound is a compound having a plurality of functional groups capable of forming an ionic bond by reacting with a carboxyl group of said water-absorbent resin.

24. The process for producing a water-absorbent resin according to claim 22,
wherein said cationic compound is a cationic polymer electrolyte and/or salt thereof.

25. The process for producing a water-absorbent resin according to claim 1, further comprising the step of drying a hydrogel after the step of polymerizing said unsaturated monomer.

26. The process for producing a water-absorbent resin according to claim 25, further comprising the step of grinding dried hydrogel after the step of drying said hydrogel.

* * * * *

UNITED STATES PATENT AND TRADEMARK OFFICE
CERTIFICATE OF CORRECTION

PATENT NO. : 6,251,960 B1
DATED : June 26, 2001
INVENTOR(S) : Kunihiko Ishizaki et al.

It is certified that error appears in the above-identified patent and that said Letters Patent is hereby corrected as shown below:

Title page,
Item [62], Related U.S. Application Data, the data that reads, "Division of application No. 08/687,377, filed on Aug. 26, 1996, now Pat. No. 5,985,944" should be -- Division of application No. 08/687,377, now Pat. No. 5,985,944, which is a 371 of PCT/JP95/02523, filed December 8, 1995. --

Signed and Sealed this

First Day of April, 2003

JAMES E. ROGAN
*Director of the United States Patent and Trademark Office*